United States Patent
Bernardo et al.

(10) Patent No.: US 11,344,506 B2
(45) Date of Patent: May 31, 2022

(54) RAPIDLY DISINTEGRATING ORAL DISSOLVABLE FILM

(71) Applicant: CURE Pharmaceutical Holding Corp., Oxnard, CA (US)

(72) Inventors: Jose Bernardo, Oxnard, CA (US); Vered Gigi, Oxnard, CA (US)

(*) Notice: Subject to any disclaimer, the term of this patent is extended or adjusted under 35 U.S.C. 154(b) by 0 days.

(21) Appl. No.: 16/508,637

(22) Filed: Jul. 11, 2019

(65) Prior Publication Data
US 2020/0016092 A1 Jan. 16, 2020

Related U.S. Application Data

(60) Provisional application No. 62/696,359, filed on Jul. 11, 2018.

(51) Int. Cl.
| | | |
|---|---|---|
| *A61K 31/05* | (2006.01) | |
| *A61K 47/34* | (2017.01) | |
| *A61K 47/32* | (2006.01) | |
| *A61K 47/38* | (2006.01) | |
| *A61K 9/70* | (2006.01) | |
| *A61K 9/00* | (2006.01) | |

(52) U.S. Cl.
CPC ............ *A61K 31/05* (2013.01); *A61K 9/0056* (2013.01); *A61K 9/7007* (2013.01); *A61K 47/32* (2013.01); *A61K 47/34* (2013.01); *A61K 47/38* (2013.01)

(58) Field of Classification Search
CPC .... A61K 9/0056; A61K 9/7007; A61K 47/34; A61K 47/32; A61K 31/05; A61K 47/38
See application file for complete search history.

(56) References Cited

U.S. PATENT DOCUMENTS

| | | | | |
|---|---|---|---|---|
| 2008/0075825 A1* | 3/2008 | Fuisz | ............ | A61K 9/7007 426/534 |
| 2011/0166240 A1* | 7/2011 | Myers | ............ | A61K 9/006 514/772.3 |
| 2011/0290694 A1* | 12/2011 | Fuisz | ............ | A61J 3/00 206/459.5 |
| 2014/0333003 A1* | 11/2014 | Allen | ............ | A61K 9/006 264/211 |

FOREIGN PATENT DOCUMENTS

| | | |
|---|---|---|
| CN | 105343887 A | 2/2016 |
| CN | 108261411 A | 7/2018 |
| WO | 2010146601 A1 | 12/2010 |
| WO | 2018004576 A2 | 1/2018 |
| WO | 2018236729 A1 | 12/2018 |

OTHER PUBLICATIONS

Prospector, title: Aquacoat® ECD; downloaded from https://www.ulprospector.com/en/na/Food/Detail/2981/331891/Aquacoat-ECD; Feb. 26, 2020. (Year: 2020).*
Evonik, title: Eudragit® E 100; downloaded from https://www.pharmaexcipients.com/wp-content/uploads/attachments/TI-EUDRAGIT-E-100-E-PO-E-12-5-EN.pdf?t=1508413942; Feb. 26, 2020. (Year: 2020).*
Ventola, title: medical applications for 3D printing: Current and Projected Uses; P&T®, vol. 39, No. 10, pp. 704-711; Oct. 2014. (Year: 2014).*
Williams, title: Polyethylene Glycol-Polyvinyl Alcohol Graft Copolymer: A Peroxide-Free Binder, American Pharmaceutical Review—The Review of American Pharmaceutical Business & Technology, pp. 1-10; Nov. 30, 2015 (Year: 2015).*
Ehtezazi et al , title: the application of 3D printing in the formulation of multilayered fast dissolving oral films; Journal of Pharmaceutical Sciences, (2017) pp. 1-10, Dec. 20, 2017 (Year: 2017).*
Unkown author, title: Kollicoat® Protect, published Jun. 2008. (Year: 2008).*
First Examination Report, Application No. 202117002338 dated Apr. 5, 2021, 6 Pages.
International Search Report and Written Opinion for related PCT Application No. PCT/US2019/041328 dated Sep. 26, 2019, 31 Pages.
Maren Preis et al., "Mechanical Strength Test for Orodispersible and Buccal Films", International Journal of Pharmaceutics 461 (2014) 22-29.
P K Lakshmi et al: "Formulation development of fast releasing oral thin films of levocetrizine dihydrochloride with Eudragit Epo and optimization through Taguchi orthogonal experimental design", Asian Journal of Pharmaceutics, vol. 5, No. 2, 2011, pp. 84-92.

* cited by examiner

*Primary Examiner* — Anna R Falkowitz

(57) ABSTRACT

The present invention provides for an oral dissolvable film that includes a rapidly dissolving binder, a film forming polymer, a moisture deterring polymer, and at least one of a first active ingredient and a second active ingredient. Also provided is a method of forming an oral dissolvable film and kits that include the oral dissolvable film. Also provided is a method of delivering one or more active ingredients to a subject that include orally administering the oral dissolvable film.

12 Claims, No Drawings

RAPIDLY DISINTEGRATING ORAL DISSOLVABLE FILM

RELATED APPLICATION

This application claims priority to U.S. Provisional Patent Application No. 62/696,359, filed Jul. 11, 2018, the contents of which are incorporated herein it their entirety.

BACKGROUND OF THE INVENTION

An oral dissolvable film (ODF) is a dosage form that uses a dissolving film or strip to administer drugs via absorption in the mouth (buccally or sublingually) and/or via the small intestines (enterically). A film is typically prepared using hydrophilic polymers that rapidly dissolve on the tongue or buccal cavity, delivering the drug to the systemic circulation via dissolution when contact with liquid (saliva) is made.

ODF drug delivery has emerged as an advanced alternative dosage form to the traditional tablets, capsules and liquids often associated with prescription and over-the-counter (OTC) medications, as well as nutraceuticals. Similar in size, shape and thickness to a postage stamp, ODF strips are designed for oral administration, with the user placing the strip on or under the tongue (sublingual) or along the inside of the cheek (buccal). These drug delivery options allow the medication to bypass the first pass metabolism thereby making the medication more bioavailable. As the strip dissolves, the drug can enter the blood stream enterically, buccally or sublingually.

Oral dissolvable films are becoming an increasingly popular dosage form for the oral administration of active ingredients. The use of ODFs can eliminate some common problems associated with oral solid-dosage forms (e.g., tablets and capsules), such as the fear or risk of choking associated with swallowing an oral solid-dosage forms, ease of transportation, difficulty in swallowing (dysphagia), the need for water intake with an oral solid-dosage forms, and/or the ability to be discrete when taking the medication.

ODFs can therefore be used for achieving clinical benefits, such as enhancing oral absorption and bioavailability and improving patient compliance. ODFs can therefore offer significant benefits to patient populations such as, e.g., geriatric and pediatric patients, as well as those suffering from a psychological, degenerative and/or neurological disorder, and those who are bedridden, emetic patients, those suffering from diarrhea, those suffering from sudden episode of allergic attacks, or coughing, and those who have an active life style. They also offer significant benefits to those patients wanting to administer the medication in a discreet, inconspicuous, unnoticeable and/or private manner, especially while in the company of another. ODFs can therefore be administered without the use of water, fulfilling the need of target population seeking convenience in drug administration, along with rapid onset of action with increased bioavailability due to bypassing the hepatic metabolism, consequently, leading to improved therapeutic response.

Just as with other dosage forms intended for oral administration, ODFs have typically been limited for use with specific active ingredients (e.g., those that are not moisture sensitive). What is needed, therefore, is an oral dissolvable film that can include additional classes of active ingredient (e.g., moisture sensitive, oxygen sensitive, pH sensitive, heat sensitive, etc.) not present in commercially manufactured ODFs, while maintaining the target aesthetics and performance characteristics of the ODF (e.g., desired content uniformity, desired thickness, and/or desired dissolution).

SUMMARY OF THE INVENTION

The present invention provides for an orally disintegrating film matrix. The orally disintegrating film matrix can be in the form of an oral dissolvable film and is suitable for delivering one or more active ingredients to a subject. The orally disintegrating film matrix includes a rapidly dissolving binder (e.g., Kollicoat® Protect), a film forming polymer (e.g., Hypromellose), optionally a moisture deterring polymer (e.g., EUDRAGIT® EPO), and optionally a pH adjusting agent (e.g., anhydrous citric acid). The orally disintegrating film matrix can further include an active ingredient (e.g., the orally disintegrating film matrix can include a first active ingredient). Alternatively, the active ingredient can be absent from the orally disintegrating film matrix (e.g., the first active ingredient can be absent from the orally disintegrating film matrix). Either way, a second active ingredient can optionally be added after the orally disintegrating film matrix is formed.

The present invention also provides for a method of forming an orally disintegrating film matrix. The orally disintegrating film matrix can be in the form of an oral dissolvable film and is suitable for delivering one or more active ingredients to a subject. The method includes: (a) contacting water, a rapidly dissolving binder (e.g., Kollicoat® Protect), a film forming polymer (e.g., Hypromellose), optionally a moisture deterring polymer (e.g., EUDRAGIT® EPO), and optionally a pH adjusting agent (e.g., anhydrous citric acid) to form a homogeneous mixture; (b) extruding the homogeneous mixture onto a substrate; and (c) curing the extruded homogeneous mixture to form an orally disintegrating film matrix (which can be in the form of an oral dissolvable film). The homogeneous mixture in (a) (alternatively referred to as a "slurry") can further include an active ingredient (e.g., the homogeneous mixture can include a first active ingredient). Alternatively, the active ingredient can be absent from the homogeneous mixture in (a) (e.g., the first active ingredient can be absent from the homogeneous mixture) and accordingly absent from the orally disintegrating film matrix. The second active ingredient can optionally be added after the orally disintegrating film matrix is formed.

The present invention also provides for an orally disintegrating film matrix in the form of an oral dissolvable film, suitable for delivering one or more active ingredients to a subject. The orally disintegrating film matrix includes a rapidly dissolving binder (e.g., Kollicoat® Protect), a film forming polymer (e.g., Hypromellose), an active ingredient, optionally a moisture deterring polymer (e.g., EUDRAGIT® EPO), and optionally a pH adjusting agent (e.g., anhydrous citric acid). A second active ingredient can optionally be added after the orally disintegrating film matrix is formed.

The present invention also provides for a kit that includes the orally disintegrating film matrix described herein (in the form of an oral dissolvable film), contained within a sealable and vapor impermeable container closure system.

The present invention also provides for a method of forming an orally disintegrating film matrix. The orally disintegrating film matrix can be in the form of an oral dissolvable film and is suitable for delivering one or more active ingredients to a subject. The method includes: (a) contacting water, a rapidly dissolving binder (e.g., Kollicoat® Protect), a film forming polymer (e.g., Hypromellose), a first active ingredient, optionally a moisture deterring polymer (e.g., EUDRAGIT® EPO), optionally a pH adjusting agent (e.g., anhydrous citric acid) to form a homogeneous mixture; (b) extruding the homogeneous mixture onto a substrate; and (c) curing the extruded homogeneous mixture to form an orally disintegrating film matrix (which can be in the form of an oral dissolvable film). Further, a second active ingredient can optionally be added after the orally disintegrating film matrix is formed. The second active ingredient can be impregnated to the orally disintegrating film matrix (e.g., via 3D printing).

The present invention also provides for a method of delivering one or more active ingredients to a subject in need thereof. The method includes administering to the subject the orally disintegrating film matrix (oral dissolvable film) described herein. The orally disintegrating film matrix can include a first active ingredient as the only active ingredient. Alternatively, the orally disintegrating film matrix can include a second active ingredient as the only active ingredient. Alternatively, the orally disintegrating film matrix can include both a first and a second active ingredient. The first active ingredient is present when the orally disintegrating film matrix is formed (e.g., present in the slurry). The second active ingredient can be impregnated to the orally disintegrating film matrix (e.g., via 3D printing) after the orally disintegrating film matrix is formed.

The orally disintegrating film matrix described herein provides the advantages of achieving one or more of the significant and advantageous features (1)-(10): the orally disintegrating film matrix is (1) formulated as an oral dissolvable film to include a therapeutically effective amount of active ingredient that is at least one of: (a) moisture sensitive, (b) oxygen sensitive, (c) pH sensitive, (d) heat sensitive, (e) light (UV) sensitive, (f) having an unpleasant taste or odor, (g) water-insoluble, and (h) present in a small quantity; (2) formulated as a "thin film" having a suitable thickness, while (3) the oral dissolvable film has a desired kinetics of erodibility. Having the dissolvable oral film be "thin," and for it to have a desired (e.g., rapid) dissolution when placed in the mouth, is advantageous at least with small children who are at risk of choking on orally administered medications, as well as those patients suffering from dysphagia. Additionally, (4) the orally disintegrating film matrix can readily be printed on (e.g., via 3D printing). This includes (5) impregnating to the orally disintegrating film matrix (e.g., via 3D printing) an active ingredient. The orally disintegrating film matrix is formulated as an oral dissolvable film to (6) contain a low level of moisture (e.g., residual solvent), (7) target a specific pH range (e.g., inclusion of acid, base, and/or buffer), (8) effectively mask the taste of the active ingredient without the use of a taste masking agent and/or sweetener, (9) while being non-hygroscopic.

In those embodiments where an active ingredient is added after the orally disintegrating film matrix is formed, (10) the orally disintegrating film matrix can be formulated and stored (over extended periods of time) as a film roll. In doing so, the added active ingredient can include those that are (a) moisture sensitive, (b) oxygen sensitive, (c) pH sensitive, (d) heat sensitive, and/or (e) light (UV) sensitive, without unduly compromising the stability, physical integrity, safety and/or effectiveness of the orally disintegrating film matrix had the orally disintegrating film matrix included such active ingredient prior to the storage of the film roll.

As described herein, various embodiments of the invention can independently include one or more of the significant and advantageous features (1)-(10) described above. Specifically, the significant and advantageous features possessed by the various embodiments can vary (or remain the same), across multiple embodiments. More specifically, the significant and advantageous features possessed by various embodiments can be the same as the significant and advantageous features possessed by other embodiments. Alternatively, the significant and advantageous features possessed by various embodiments can be different from the significant and advantageous features possessed by other embodiments. More specifically, a significant and advantageous feature possessed by any specific embodiment can be independent of, and mutually exclusive of, any significant and advantageous feature possessed by any other embodiment.

DETAILED DESCRIPTION OF THE INVENTION

The present invention provides for an orally disintegrating film matrix that includes a rapidly dissolving binder and film forming polymer. The present invention also provides for an orally disintegrating film matrix that includes a first active ingredient; a rapidly dissolving binder; and a film forming polymer.

The present invention provides for a method of forming an orally disintegrating film matrix that includes: (a) contacting water, a rapidly dissolving binder, and a film forming polymer, to form a homogeneous mixture; (b) extruding the homogeneous mixture onto a substrate; (c) curing the extruded homogeneous mixture to form the orally disintegrating film matrix; and (d) optionally sizing the orally disintegrating film matrix to a desired surface area.

The present invention also provides for a method of forming an orally disintegrating film matrix that includes: (a) contacting water, a rapidly dissolving binder, and a film forming polymer, to form a homogeneous mixture; (b) extruding the homogeneous mixture onto a substrate; (c) curing the extruded homogeneous mixture to form the orally disintegrating film matrix; (d) optionally impregnating a second active ingredient to the orally disintegrating film matrix; and (e) optionally sizing the orally disintegrating film matrix to a desired surface area.

The present invention also provides for a method of forming an orally disintegrating film matrix that includes: (a) contacting water, a rapidly dissolving binder, and a film forming polymer, to form a homogeneous mixture; (b) extruding the homogeneous mixture onto a substrate; (c) curing the extruded homogeneous mixture to form the orally disintegrating film matrix; (d) storing the orally disintegrating film matrix, transporting the orally disintegrating film matrix, or a combination thereof, (e) optionally impregnating a second active ingredient to the orally disintegrating film matrix; and (f) optionally sizing the orally disintegrating film matrix to a desired surface area.

The present invention also provides for a method of forming an orally disintegrating film matrix that includes: (a) contacting water, a first active ingredient, a rapidly dissolving binder, and a film forming polymer, to form a homogeneous mixture; (b) extruding the homogeneous mixture onto a substrate; (c) curing the extruded homogeneous mixture to form the orally disintegrating film matrix; and (d) optionally sizing the orally disintegrating film matrix to a desired surface area.

The present invention also provides for a method of forming an orally disintegrating film matrix that includes: (a) contacting water, a first active ingredient, a rapidly dissolving binder, and a film forming polymer, to form a homogeneous mixture; (b) extruding the homogeneous mixture onto a substrate; (c) curing the extruded homogeneous mixture to form the orally disintegrating film matrix; (d) optionally impregnating a second active ingredient to the orally disintegrating film matrix; and (e) optionally sizing the orally disintegrating film matrix to a desired surface area.

The present invention also provides for a method of forming an orally disintegrating film matrix that includes: (a) contacting water, a first active ingredient, a rapidly dissolving binder, and a film forming polymer, to form a homogeneous mixture; (b) extruding the homogeneous mixture onto a substrate; (c) curing the extruded homogeneous mixture to form the orally disintegrating film matrix; (d) storing the orally disintegrating film matrix, transporting the orally disintegrating film matrix, or a combination thereof, (e) optionally impregnating a second active ingredient to the orally disintegrating film matrix; and (f) optionally sizing the orally disintegrating film matrix to a desired surface area.

The present invention also provides for a kit that includes: (a) an orally disintegrating film matrix (oral dissolvable film) described herein, or an orally disintegrating film matrix (oral dissolvable film) obtained by the method described herein; and (b) a sealable and vapor impermeable container closure system; wherein the orally disintegrating film matrix (oral dissolvable film) is contained within the sealable and vapor impermeable container closure system.

The present invention also provides for a method of delivering an active ingredient to a subject in need thereof. The method includes orally administering to the subject an orally disintegrating film matrix described herein, or an orally disintegrating film matrix obtained by the method described herein.

Definitions

The term the following terms have the meanings ascribed to them unless specified otherwise.

The term "moisture sensitive active ingredient" refers to an active ingredient that will react with water or moisture, under normal ambient conditions (e.g., at about 20° C.). The moisture sensitive active ingredient can degrade when directly contacting water or moisture. Thus, moisture-sensitive active ingredients often are not formulated to be in direct contact with water during the manufacturing of the dosage form. This holds true as well with any direct contact with water or moisture during the extended periods of time associated with the storage and shipment of the dosage form.

The term "oxygen sensitive active ingredient" refers to an active ingredient that will react with oxygen, under normal ambient conditions (e.g., at about 20° C.). The oxygen sensitive active ingredient can degrade when directly contacting oxygen. Thus, oxygen-sensitive active ingredients often are not formulated to be in direct contact with oxygen during the extended periods of time associated with the storage and shipment of the dosage form.

The term "pH sensitive active ingredient" refers to an active ingredient susceptible to degradation at specific pH ranges, under normal ambient conditions (e.g., at about 20° C.). Thus, pH-sensitive active ingredients often are not formulated to be at specific pH ranges during the manufacturing of the dosage form. This holds true as well with any pH ranges during the extended periods of time associated with the storage and shipment of the dosage form. For example, specific pH sensitive active ingredients may be prone to degradation at lower pH ranges (e.g., below 7). Such pH sensitive active ingredients should avoid direct contact with acids or acidic compounds. Likewise, specific pH sensitive active ingredients may be prone to degradation at higher pH ranges (e.g., above 7). Such pH sensitive active ingredients should avoid direct contact with bases or basic compounds.

The term "heat sensitive active ingredient" refers to an active ingredient susceptible to degradation at elevated temperatures (e.g., above about 40° C.). Thus, heat-sensitive active ingredients often are not formulated at elevated temperatures during the manufacturing of the dosage form. This holds true as well with any elevated temperatures during the extended periods of time associated with the storage and shipment of the dosage form.

The term "light (UV) sensitive active ingredient" refers to an active ingredient susceptible to degradation upon extended exposure to light (UV), under normal ambient conditions (e.g., at about 20° C.). Thus, light-sensitive active ingredients often are not formulated to be in direct contact with light (UV) (at least not extended exposures) during the manufacturing of the dosage form. This holds true as well with any direct exposure to light (UV) during the extended periods of time associated with the storage and shipment of the dosage form.

The term "orally disintegrating film matrix" refers to a polymeric film matrix formulated for administration in the oral cavity to disintegrate over a desired period of time. The orally disintegrating film matrix is configured to contain one or more active ingredients. The active ingredient(s) can be added after the orally disintegrating film matrix is formed (e.g., by impregnating the active ingredient(s) to the orally disintegrating film matrix). The active ingredient(s) can alternatively be added during the manufacture of the orally disintegrating film matrix (e.g., by forming a slurry containing the active ingredient(s) and subsequently curing to form the film). The active ingredient(s) can alternatively be added both during the manufacture of the orally disintegrating film matrix as well as after the orally disintegrating film matrix is formed.

The term "rapidly dissolving binder" refers to a binder capable of dissolving in saliva, when placed in the mouth, in a relatively short period of time. Typically, the rapidly dissolving binder will dissolve within 20 seconds when placed in the mouth. Additionally, when present in the orally disintegrating film matrix in the desired amount, the rapidly dissolving binder will effectively dissolve in saliva, allowing the saliva to thereby dissolve and/or disintegrate the remaining portions of the orally disintegrating film matrix (and the remaining substances present therein). As a binder, the substance is capable of binding the other substances present therein (e.g., present in the slurry) during and after formation of the orally disintegrating film matrix, effectively keeping it intact prior to use. One suitable rapidly dissolving binder is Kollicoat® Protect (polyvinyl alcohol (PVA)-polyethylene glycol (PEG) copolymer and polyvinyl alcohol (PVA)).

The term "film forming polymer" refers to polymers capable of forming an oral film. Typically, the film forming polymer will be hydrophilic and water-soluble. One suitable film forming polymer is Hypromellose (hydroxypropyl methyl cellulose (HPMC)).

The term "moisture content" refers to the amount of water present in a substance (e.g., orally disintegrating film matrix). The water can be bound, unbound, or a combination thereof. The amount of water present therein can conveniently be expressed as a weight percentage of the substance.

The term "oral cavity" refers to the opening through which humans take in food and issue vocal sounds. The oral cavity is the first portion of the alimentary canal that receives food and produces saliva. The oral mucosa is the mucous membrane epithelium lining the inside of the mouth.

The term "disintegrate" or "disintegration" refers to a substance (e.g., orally disintegrating film matrix) breaking up or falling apart. The substance will lose cohesion or strength and can fragment into smaller pieces. When placed in the mouth, the substance will break apart in the saliva. The terms "disintegrate" or "disintegration" encompass the term "dissolution," to the extent that the substance may not specifically fall apart (e.g., fragment into smaller pieces), but may simply dissolve in saliva when placed in the mouth. If so, a substance having a dissolution of a specified period of time is understood to also have a disintegration of no more than that same specified period of time.

The term "moisture deterring polymer" refers to a polymer, when formulated in an orally disintegrating film matrix, will substantially deter water or moisture from being adsorbed. One suitable moisture deterring polymer is Eudragit® EPO (aminoalkyl methacrylate copolymers).

The term "Kollicoat® Protect" refers to the combination of water-soluble Kollicoat® IR and polyvinyl alcohol (PVA). Kollicoat® Protect is polyvinyl alcohol (PVA)-polyethylene glycol (PEG) copolymer and polyvinyl alcohol (PVA) and is commercially available from BASF (Ludwigshafen, DE). This instant release coating material is highly impermeable to water—making it suitable for moisture-sensitive active ingredients and greatly increasing formulation stability. The polymers are embedded in one another to such an extent that they cannot readily separate. The powder has good flowability and dissolves rapidly in water. Kollicoat® Protect provides, e.g., moisture protection, stability, and taste masking effect.

The term "Kollicoat® IR" refers to a polyvinyl alcohol (PVA)-polyethylene glycol (PEG) graft copolymer. Kollicoat® IR is commercially available from BASF (Ludwigshafen, DE).

The term "Eudragit® EPO" refers to a ready mix powder containing EUDRAGIT® E 100, Sodium lauryl sulfate (SLS), Talc, Silicon dioxide, and Stearic acid. Eudragit® EPO is commercially available from Evonik (Essen, Germany). Eudragit® EPO (EE) includes a cationic polymer having a mean relative molecular mass of about 150,000, which prepared by copolymerization of butyl methacrylate, 2-dimethylaminoethylmethacrylate, and methyl methacrylate. The ratio of dimethylaminoethyl methacrylate groups to butyl methacrylate and methyl methacrylate groups is about 2 to 1:1. As such, Eudragit® EPO includes aminoalkyl methacrylate copolymers. Eudragit® EPO is a cationic copolymer based on dimethylaminoethyl methacrylate, butyl methacrylate, and methyl methacrylate. The Chemical/IUPAC name is Poly(butyl methacrylate-co-(2-demethyl-aminoeethyl) methacrylate-co-methyl methacrylate) 1:2:1.

The term "Eudragit® E 100" refers to a cationic copolymer based on dimethylaminoethyl methacrylate, butyl methacrylate, and methyl methacrylate with a ratio of 2:1:1. The monomers are randomly distributed along the copolymer chain. Based on SEC method the weight average molar mass (Mw) of EUDRAGIT® E 100; EUDRAGIT® EPO and EUDRAGIT® E 12,5 is approximately 47,000 g/mol. Eudragit® E 100 is commercially available from Evonik (Essen, Germany).

The term "printed indicia" refers to any words or images present on the orally disintegrating film matrix. The words can include, e.g., at least one of a letter, word, marking, design, logo, symbol, image, product name, active ingredient(s), strength, manufacturer company name, marketing company name, manufacturer company logo, marketing company logo, instructions of use, and product warnings.

The term "subject" refers to living organisms such as humans, dogs, cats, and other mammals. Administration of the active ingredients included in the orally disintegrating film matrices of the present invention can be carried out at dosages and for periods of time effective for the treatment of the subject. In some embodiments, the subject is a human. Unless otherwise specified, the human subject can be a male or female, and can further be an adult, adolescent, child, toddler, or infant.

The term "transmucosal," as used herein, refers to any route of administration via a mucosal membrane or mucosal surface. Examples include, but are not limited to, buccal, sublingual, nasal, vaginal, and rectal.

The term "buccal administration" refers to a topical route of administration by which a drug held or applied in the buccal area (in the cheek) diffuses through the oral mucosa (tissues which line the mouth) and enters directly into the bloodstream. Buccal administration may provide better bioavailability of some drugs and a more rapid onset of action compared to oral administration because the medication does not pass through the digestive system and thereby avoids first pass metabolism.

The term "buccal space" (also termed the buccinator space) refers to a fascial space of the head and neck (sometimes also termed fascial tissue spaces or tissue spaces). It is a potential space in the cheek, and is paired on each side. The buccal space is superficial to the buccinator muscle and deep to the platysma muscle and the skin. The buccal space is part of the subcutaneous space, which is continuous from head to toe.

The term "oral mucosa" refers to the mucous membrane lining the inside of the mouth and consists of stratified squamous epithelium termed oral epithelium and an underlying connective tissue termed lamina propria. Oral mucosa can be divided into three main categories based on function and histology: (1) Masticatory mucosa, keratinized stratified squamous epithelium, found on the dorsum of the tongue, hard palate and attached gingiva; (2) Lining mucosa, nonkeratinized stratified squamous epithelium, found almost everywhere else in the oral cavity, including the: (a) Buccal mucosa refers to the inside lining of the cheeks and floor of the mouth and is part of the lining mucosa; (b) Labial mucosa refers to the inside lining of the lips and is part of the lining mucosa; and (c) Alveolar mucosa refers to the lining between the buccal and labial mucosae. It is a brighter red, smooth and shiny with many blood vessels, and is not connected to underlying tissue by rete pegs; and (3) Specialized mucosa, specifically in the regions of the taste buds on lingual papillae on the dorsal surface of the tongue that contains nerve endings for general sensory reception and taste perception.

The term "sublingual administration," from the Latin for "under the tongue," refers to the pharmacological route of administration by which substances diffuse into the blood through tissues under the tongue. When a drug comes in contact with the mucous membrane beneath the tongue, it is absorbed. Because the connective tissue beneath the epithelium contains a profusion of capillaries, the substance then diffuses into them and enters the venous circulation. In contrast, substances absorbed in the intestines are subject to first-pass metabolism in the liver before entering the general circulation. Sublingual administration has certain advantages over oral administration. Being more direct, it is often faster, and it ensures that the substance will risk degradation only by salivary enzymes before entering the bloodstream, whereas orally administered drugs must survive passage through the hostile environment of the gastrointestinal tract, which risks degrading them, by either stomach acid or bile, or by enzymes such as monoamine oxidase (MAO). Furthermore, after absorption from the gastrointestinal tract, such drugs must pass to the liver, where they may be extensively altered; this is known as the first pass effect of drug metabolism. Due to the digestive activity of the stomach and intestines, the oral route is unsuitable for certain substances.

The term "gingival administration" refers to the pharmacological route of administration by which substances diffuse into the blood through tissues in the gums. The gums or gingiva (plural: gingivae), consist of the mucosal tissue that lies over the mandible and maxilla inside the mouth.

The term "enteral administration" refers to a drug administration via the human gastrointestinal tract. Enteral administration involves the esophagus, stomach, and small and large intestines (i.e., the gastrointestinal tract). Methods of administration include oral and rectal. Enteral administration may be divided into three different categories, depending on the entrance point into the GI tract: oral (by mouth), gastric (through the stomach), and rectal (from the rectum). (Gastric introduction involves the use of a tube through the nasal passage (NG tube) or a tube in the belly leading directly to the stomach (PEG tube). Rectal administration usually involves rectal suppositories.) Enteral medications come in various forms, including, e.g., tablets to swallow, chew or dissolve in water; capsules and chewable capsules (with a coating that dissolves in the stomach or bowel to release the medication there), oral soluble films, time-release or sustained-release tablets and capsules (which release the medication gradually), osmotic delivery systems, powders or granules, and liquid medications or syrups.

The term "oral administration" or "PO" refers to a route of administration where a substance is taken through the mouth. Many medications are taken orally because they are intended to have a systemic effect, reaching different parts of the body via the bloodstream.

The term "pharmaceutically acceptable" refers to those compounds, excipients, active ingredients, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The unit dosage form (e.g., oral dissolvable film) can be administered, e.g., to a human patient in need of a treatment of a particular disease or disorder. Selection of the active ingredient(s) within the unit dosage form described herein will be dependent upon the particular disease or disorder to be treated. The Physician's Desk Reference, 2018 Edition; The Merck Index, 15th Edition (2013); United States Pharmacopeia (USP) (2018); National Formulary as the USP-NF (2018); and the International Pharmacopoeia (Pharmacopoeia Internationalis, Ph. Int.) (2017) provide a description of the diseases or disorders that specific active ingredients have been approved for (e.g., by the U.S. FDA or EMA), in the marketing and sale of the product (e.g., within the United States or Europe). As such, a skilled artisan can look to such references for guidance in the selection of the active ingredient(s) to be present within the unit dosage form, based upon the treatment of the specific disease or disorder of particular interest (and vice-versa).

The term "active ingredient" is used to include any "drug," "bioactive agent," "preparation," "medicament," "therapeutic agent," "physiological agent," "nutraceutical," or "pharmaceutical agent" and includes substances for use in the treatment of a disease or disorder. Dietary supplements, vitamins, functional foods (e.g., ginger, green tea, lutein, garlic, lycopene, capsaicin, and the like), cannabinoids, and terpenes are also included in this term. Standard references such as, e.g., The Physician's Desk Reference, 2018 Edition; The Merck Index, 15th Edition (2013); and United States Pharmacopeia (USP) (2018) provide a description of specific active ingredients.

Oral Dissolvable Film

Oral dissolvable films (alternatively known as ODFs, oral films, orally dissolving film strips, edible films, edible strips, oral film strips, oral drug strips, buccal films, sublingual films, oral soluble films, etc.) refer to a unit dosage form in which a film is administered in the oral cavity and disintegrates over a desired period of time.

The term "oral dissolvable film" refers to a film specifically configured, formulated, and suitable for oral administration. The oral dissolvable film is a unit dosage form composed of one or more pharmaceutically acceptable ingredients that are edible and/or ingestible. The oral dissolvable film can be configured for multi- or unidirectional release. Similar in size and shape to a postage stamp, oral dissolvable films are designed for oral administration, with the user placing the strip on the tongue (enteric), under the tongue (sublingual), against the inside of the cheek (buccal), or on the gums (gingival). Aside from the enteric route, these drug delivery options allow the medication to bypass the first pass metabolism thereby making the medication more bioavailable. As the film dissolves, the drug can enter the blood stream enterically, buccally, gingivally, or sublingually. As such, the oral dissolvable film dissolves in the oral cavity (e.g., under the tongue), delivering the drug to the systemic circulation via dissolution when contact with saliva is made. Oral dissolvable film drug delivery accordingly uses a dissolving film matrix to administer drugs via absorption in the mouth (buccally, sublingually, or gingivally) and/or via the small intestines (enterically). Especially for drugs which are metabolized extensively by the first-pass effect, oral dissolvable films described herein provide an opportunity for a faster-acting and better absorption profile.

When systemic delivery (e.g., transmucosal delivery) is desired, the treatment site may include any area in which the adherent film described herein is capable of maintaining a desired level of pharmaceutical in the blood, lymph, or other bodily fluid. Typically, such treatment sites include the oral mucosa (e.g., on the tongue, under the tongue, against gums, against the cheek, etc.).

The oral dissolvable films described herein include a polymeric matrix formed from a film-forming polymer, binder, solvent, and one or more active ingredients (e.g., first active ingredient, second active ingredient, or combination thereof). Optional additional excipients (alternatively referred to as "additives") used to manufacture the oral dissolvable film can include, e.g., one or more of plasticizer, filler, bulking agent, saliva stimulating agent, stabilizing and thickening agent, gelling agent, flavoring agent, taste masking agent, coloring agent, pigment, lubricant, release modifier, adjuvant, sweetening agent, solubilizer & emulsifier, fragrance, emulsifier, surfactant, pH adjusting agent, buffering agent, lipid, glidant, stabilizer, antioxidant, anti-tacking agent, humectant, and preservative. Suitable excipients that can be used in the formulation of oral films are described in, e.g., Lachman, et al., "The Theory and Practice of Industrial Pharmacy," $4^{th}$ Edition (2013); Rowe et al., "Handbook of Pharmaceutical Excipients," 8th Edition (2017); and Remington, "The Science and Practice of Pharmacy," 22nd Edition (2015). From the regulatory perspectives, all excipients used in the formulation of the oral films described herein should preferably be approved for use in oral pharmaceutical dosage forms.

In particular embodiments, the orally disintegrating film matrix is an oral dissolvable film. In such embodiments, the orally disintegrating film matrix is a unit dosage form in which the film matrix can be administered in the oral cavity to disintegrate over a desired period of time. However, in alternative specific embodiments, the orally disintegrating film matrix can be an oral dissolvable film, but will not necessarily exist in a unit dosage form. For example, in some embodiments, the orally disintegrating film matrix will not necessarily be sized to a desired surface area, but may exist as a roll (alternatively known as a bulk roll), where it can be stored for extended periods of time. In additional embodiments, the orally disintegrating film matrix can optionally include a first active ingredient, but may be formulated and configured to later include a second active ingredient.

As such, distinction can be made between an orally disintegrating film matrix and an oral dissolvable film, such that in specific embodiments, the former may not contain any active ingredient, the former may contain a first active ingredient but not a second active ingredient, and/or the former may not exist in a unit dosage form (e.g., may not be sized to a desired surface area). However, as described herein, in specific embodiments, the orally disintegrating film matrix can be an oral dissolvable film. Exemplary embodiments are illustrated below.

plastic laminate sheet. Alternatively, individual films can be packaged such that they are in direct contact with one another (e.g., they are stacked on top of one another). The use of a powder coating, for example, can decrease the likelihood that individual films will stick or adhere to one another. The multiple films that are packaged together can be located within a dispenser (e.g., cassette). Such a dispenser can contain a full supply of the medication typically prescribed for the intended therapy, but due to the thinness of the film and package, will likely be smaller and more convenient than traditional bottles used for tablets, capsules and liquids.

Administration of the Oral Dissolvable Film

Generally, the oral dissolvable film will be administered as indicated by the instructions and/or the prescribing medical practitioner. Preferably, the oral dissolvable film should not be applied to areas of the mouth with any open sores or lesions. The oral dissolvable film should also not be used if the package seal is broken or the oral film is cut or damaged. Preferably, with clean and dry hands, the oral dissolvable film is applied immediately after removal from the sealed package. The prescribing instructions may also indicate that the patient use the entire oral dissolvable film and should not cut or tear it.

Oral dissolving films that are designed to be applied on top of the tongue can effectively deliver the active ingredient via the enteral route. The patient will typically drink water to moisten the mouth. This may help the film stick and

| Film construct | Orally disintegrating film matrix or oral dissolvable film |
|---|---|
| First active ingredient + second active ingredient + sized | oral dissolvable film |
| First active ingredient + no second active ingredient + sized | oral dissolvable film |
| First active ingredient + no second active ingredient + not sized | orally disintegrating film matrix or oral dissolvable film (depends whether or not $2^{nd}$ active ingredient will be added) |
| First active ingredient + second active ingredient + not sized | oral dissolvable film |
| No first active ingredient + no second active ingredient + not sized | orally disintegrating film matrix ($2^{nd}$ active ingredient will presumably be added) |
| No first active ingredient + second active ingredient + not sized | oral dissolvable film |
| No first active ingredient + second active ingredient + sized | oral dissolvable film |
| No first active ingredient + no second active ingredient + sized | N/A |

Packaging of Oral Dissolvable Films

Packing considerations are important for storage, protection and stability of dosage forms. Packaging for oral dissolvable films typically includes foil paper or plastic pouches, single pouch, aluminum pouch, blister packaging with multiple units and barrier films. Barrier films are most commonly used for those drugs which are extremely moisture sensitive. In specific embodiments, the packaging will be child-resistant (e.g., child-resistant foil packages or child-resistant polyester/foil laminated pouches). Primary packaging made of a sealing pouch affords enough space for logos, codes, instructions, strengths, or other information. The films can be manufactured by a laminating process.

Desirably, a series of oral dissolvable films can be packaged together in accordance with the prescribed regimen or treatment, e.g., a 10-90 day supply, depending on the particular therapy. The individual films can be packaged on a backing and peeled off for use. Specifically, each film can be individually wrapped in a pouch or between foil and/or dissolve more easily. The orally dissolving film is then placed on top of the tongue where it dissolves and is swallowed, with or without water.

Buccal films provide for the transmucosal delivery of active ingredient. When the oral dissolvable film is a buccal film, the patient will typically wet the inside of the cheek or rinse the mouth with water to wet the area for placement of the buccal film. This may help the film stick and dissolve more easily. The buccal film can then be applied against the inside of the cheek.

The entire buccal film can be held in place with clean, dry fingers for about 5 seconds and then left in place on the inside of the cheek until fully dissolved. Preferably, the buccal film should not be manipulated with the tongue or finger(s). The buccal film should adhere to the moist buccal mucosa and completely dissolve after application. Preferably, eating food or drink should also be avoided until the buccal film has dissolved. A buccal film, if chewed or swallowed, may result in lower peak plasma concentrations and lower bioavailability than when used as directed.

When the oral dissolvable film is a sublingual film, the patient will typically drink water to moisten the mouth. This may help the film stick and dissolve more easily. The sublingual film can then be applied under the tongue, close to the base, either to the left or the right of the center. The entire sublingual film can be held in place until fully dissolved. Preferably, the sublingual film should not be manipulated with the tongue or finger(s). The sublingual film should adhere to the moist sublingual mucosa and completely dissolve after application. Preferably, eating food or drink should also be avoided until the sublingual film has dissolved. A sublingual film, if chewed or swallowed, may result in lower peak plasma concentrations and lower bioavailability than when used as directed.

Dosages

The active ingredient(s) will preferably be present in the oral dissolvable film in a "therapeutically effective amount." The term "therapeutically effective amount" or "effective amount" means an amount of active ingredient, present in the oral dissolvable film, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

When an active ingredient is introduced to the oral dissolvable film, the amount of active ingredient per unit area is determined by the uniform distribution of the oral film. For example, because the oral dissolvable films exist as individual unit dosage forms, the amount of the active ingredient in the unit dosage form can be known with a great deal of accuracy. This is achieved because the amount of the active ingredient in a given area is substantially identical to the amount of active ingredient in an area of the same dimensions (i.e., length and width) in another part of the oral film. The accuracy in dosage is particularly advantageous when an accurate and precise amount of active ingredient is desirable.

The oral dissolvable films described herein are capable of accommodating a wide range of amounts of the active ingredient. The films are therefore capable of providing a relatively precise and accurate dosage amount (determined by the size of the film and concentration of the active in the slurry), regardless of whether the required dosage is high or low. For example, the oral dissolvable films described herein can include the active ingredient in up to about 10 mg/cm$^2$.

Methods of Manufacturing

The manufacture of orally dissolving films can be carried out by various methods such as: (1) casting (e.g., solvent casting or semi-solid casting), (2) extrusion (e.g., hot melt extrusion or solid dispersion), and (3) rolling. The specific processing parameters can be selected based upon the desired product specifications. In preferred embodiments, the methods include those described below and preferably comply with US FDA good manufacturing practice (GMP) guidelines.

Briefly stated, the methods of manufacturing the oral dissolvable film can include (1) dispensing raw materials to provide dispensed ingredients, (2) mixing the dispensed ingredients to provide mixed ingredients (commonly referred to as a "slurry" or "product"), (3) curing the slurry to provide a work-in-process (WIP) product (commonly referred to as a "bulk roll"), and (4) converting and packaging the bulk roll to provide packaged product. Alternatively, (5) packaging of the work in process (WIP) product ("bulk roll") can be carried out, such that the bulk roll is made commercially available.

The dispensing of raw materials, to provide dispensed ingredients, typically includes weighing the raw materials to be used in the production. The dispensing is preferably carried out with cleaned and sanitized equipment. Additionally, all raw material containers for use are preferably wiped down (e.g., with 70/% v/v ethyl alcohol), prior to use. Raw materials are preferably dispensed from inside a dispensing room in a fume hood, one at a time, with no other raw materials present in the room. Gloves are preferably wiped down (e.g., with 70% v/v ethyl alcohol) in between the weighing of each raw material to protect against cross-contamination. All surfaces, bench tops, balances, etc. are preferably cleaned, after the completion of weighing one batch, and before weighing ingredients of another batch. Preferably, after each ingredient for a particular batch is weighed, it is placed in a labeled container and sealed. The ingredient(s) contained within the sealed container(s) can be used immediately, or can be staged, prior to use, for an extended period of time (e.g., up to about 1 month).

The mixing of the dispensed ingredients to provide mixed ingredients typically includes the use of a high shear mixer. For example, the mixer can be a Scott Turbon Mixer, which is commercially available from, e.g., Rodem® (Cincinnati, Ohio). Typically, two mixer systems of similar capabilities can be used in the manufacturing process. One system can be portable and the other one can be fixed. The mixing is preferably carried out with cleaned and sanitized equipment.

The portable system can include one all-stainless steel, non-jacketed, mixing vessel (e.g., 60 gallon) with an attached motor (e.g., 10 amp) and a mixing head (e.g., Type A). The fixed system can be a floor mounted, belt-type, hydraulic lift, all stainless-steel system with a motor (e.g., 20 amp) and a mixer head (e.g., Type A). Two vessels can also be part of the fixed system. One jacketed tank (e.g., 50 gallons) and one non-jacketed tank (e.g., 60 gallons). Both mixers can be controlled, e.g., via an Allen Bradley variable frequency drive (VFD) with power adjustments across the 60 Hz range.

Prior to the mixing, the dispensed ingredients can be heated or cooled. Additionally, during the mixing, the dispensed ingredients can be heated or cooled. Alternatively, the mixing of the dispensed ingredients can be carried out at about room temperature.

The ingredients can be added to the mixer in any suitable order, at a suitable mixing speed, and over any suitable period of time, provided the mixing can completely be carried out and the mixed ingredients are effectively obtained.

Preferably, the mixing of the dispensed ingredients is carried out at a mixing speed, temperature, and for a period of time to obtain a solution (the mixed ingredients or slurry) that is uniform and homogeneous with a consistency that allows for further processing.

Once the mixed ingredients or slurry is obtained, it can be used immediately, it can be transferred to a holding vessel, or it can remain in the mixing tank (preferably covered to control solvent loss) for later processing.

After use and in between batches, the mixing equipment (e.g., mixer) is preferably cleaned, rinsed, sanitized, and dried. Any suitable cleaning product can be used. For example, 100 ml of 7× Cleaning Solution, available from MP Biomedicals (Santa Ana, Calif.) can be used in the mixing tank(s). The cleaning is preferably followed by draining and rinsing with USP purified water. The rinsing is preferably followed by sanitizing which can include wiping external and internal surfaces with 70/% v/v ethanol.

The curing of the slurry to provide a work in process (WIP) product ("bulk roll") typically includes the use of appropriate equipment, such as drying and curing systems. One suitable drying and curing system is an ASI Dryer System, available from Advanced Systems, Inc. (ASI) (Green Bay, Wis.). The curing of the slurry is preferably carried out with cleaned and sanitized equipment.

The ASI Dryer System includes three major components: (1) the unwind station, (2) the dryer, (3) the winding station, and (4) precision modular coating head with an unwind, pull roll system and the pump cart. The unwind station automatically controls tension. The controller maintains web tension regardless of roll diameter. Torque is controlled by a friction brake. A cantilevered airshaft is supported by a heavy-duty bearing housing. The dryer is a single zone high efficiency flotation drying system with an internal plenum that includes a dedicated supply fan. The supply fan provides air to the air bars at a pre-determined nozzle outlet velocity as needed for the application. These air bars are used to both dry the slurry (also referred to as "product," before and/or after curing) and support/convey the web in the dryer. The winding station collects the product after the dryer. An automatic edge guide system properly guides the web through the process. Dual airshafts are cantilevered and supported by a heavy-duty bearing housings.

For the curing process, briefly stated, the substrate initially can enter the unwinding station. The substrate can then proceed though the product extruder. Once coated with the slurry, the substrate can then proceed through the dryer where the slurry is at least partially cured. In specific embodiments, the substrate can proceed through the dryer where the slurry is essentially completely cured. As the cured product exits the dryer, the moisture content of the sample can be taken by the moisture analyzer. If desired, a powder coating (with the use of a powder dispenser) can be applied to the surface of the cured product. The cured product can then be rewound into a bulk roll.

Typically, a roll of substrate is placed in the unwinding station and tension is applied to the line. Any suitable substrate can be used, such as, e.g., Polyethylene Terephthalate (PET) or siliconized paper. PET is a thermoplastic polymer resin of the polyester family used as the substrate when coating and drying the product. Likewise, siliconized paper is a stable, release paper manufactured with two sides of polyethylene and coated with silicon polymer on one side used as the substrate when coating and drying the product.

The substrate can be threaded through the unwind station, then the product extruder, and then through the dryer. A powder dispenser can optionally be present between the over and rewinder. If applicable, the substrate can then be threaded through the powder applicator. A moisture analyzer can optionally be present between the oven and the powder dispenser. If desired, moisture content of the sample can be taken by the moisture analyzer. The substrate can then be threaded through the re-winder station.

The product can be applied into the extruder, where the substrate is coated with the product. A knife can optionally be present on the product extruder. Moisture content and weight of the product can be monitored. Product weight and moisture are examined throughout the drying process as leading indicators to inform the following step of converting the bulk roll.

After use and in between batches, the curing equipment (e.g., extruder of the drying and curing system) is preferably cleaned, rinsed, sanitized, and dried. Any suitable cleaning product can be used. For example, 100 ml of 7× Cleaning Solution, available from MP Biomedicals (Santa Ana, Calif.) can be used in the extruder box. Additional commercially available cleaning agents are available from, e.g., Steris (Minneapolis, Minn.) such as CIP 100 and CIP 200. The cleaning is preferably followed by draining and rinsing with water. The rinsing is preferably followed by sanitizing which can include wiping external and internal surfaces with 70% v/v ethanol.

The relevant curing parameters (e.g., curing temperature, velocity of coated substrate through the dryer, etc.) can be selected based upon the desired product specifications and slurry rheology. For example, the air temperature inside the oven can be about 100° F. to about 350° F. Additionally, the air nozzle velocity can be set to about 3000 feet per second to about 7000 feet per second. Likewise, the velocity of coated substrate through the dryer can be up to about 6 feet per minute (fpm), depending upon slurry solids content, thickness and residual moisture target.

The cured product (bulk roll) prior to converting is subjected to slitting process in which the edges are trimmed to produce a specific web width in accordance with the converting machine capabilities. This process removes any edge or shrinkage defects, and allows for precision in cutting the roll to specific length and width measurements.

The converting and packaging of the bulk roll to provide packaged product typically includes the use of appropriate equipment, such as a DeltaModTech Press or Doyen converting and packaging machine, commercially available from, e.g., Delta ModTech (Minneapolis, Minn.) or Optima Machinery Corporation (Green Bay, Wis.). The converting and packaging of the bulk roll is preferably carried out with cleaned and sanitized equipment.

Briefly stated, the converting and packaging can include: (1) pre-cleaning, (2) laminate installation, (3) product roll installation, (4) converting, (5) sachet forming, (6) heat sealing and (7) post cleaning. Prior to starting the converting process, all product contact surfaces (e.g., Hartnett Gravure printer rollers, release liner selvage rewind unit which includes all rollers and dancer arm, multi-lane slitting assembly, slitter anvil, lane spreading assembly, chute and guide rollers, crush cut knife station, cutting blades, and vacuum anvil) can preferably be wiped with 70% v/v ethanol.

After the pre-cleaning, printed laminate with product information and product rolls can be loaded on the converter machine and threaded through the machine. After the machine has been properly set-up with laminate, testing can be done to confirm sachet proper alignment, complete sealing with first article testing and cutting. Following successful set-up product roll processing can be carried out to produce individual strips sealed in between the front and back portion of the laminate. Laser or thermal printers can be used for lot numbering and expiration dating on the sachets. In addition, serialization using a 2D bar code, GTIN number and ISO labeling for lot and expiry can be performed.

The coated substrate can be cut to a desired dimension. Preferably, the desired dimension is suitable for administration to the patient as a unit dosage form (e.g., 2"×3" oral dissolvable film). Alternatively, the bulk roll can be placed in a hermetically bag and sealed, for further processing or to be made commercially available.

After use and in between batches, the converting and packaging equipment is preferably cleaned, rinsed, sanitized, and dried. Any suitable cleaning product can be used. For example, 100 ml of 7× Cleaning Solution, available from MP Biomedicals (Santa Ana, Calif.) can be used. The cleaning is preferably followed by rinsing with water to remove residuals. The rinsing is preferably followed by sanitizing which can include wiping external and internal surfaces with 70% v/v ethanol.

For example, the following parts of the converting and packaging equipment can be cleaned and sanitized: Hartnett Gravure printer, splicing table located above the selvage rewind, selvage rewind area including the rollers and the dancer arm, multi-lane slitting assembly and the secondary dancer arm along with the rollers, slitter, slitting grooves, product pull wheels located after the slitter assembly, lane spreading assembly, chute, tensionless loop tool, guide rollers, crush cut knife station, cut-off blades, blade backing plate, blade holders, blades, hardened vacuum anvil, rotary shear slitter, and slitting blades.

Characterization and Evaluation

Once manufactured, the oral dissolvable film can enter the global marketplace where it is distributed and ultimately consumed by the subject. Prior to entering the global marketplace, batch samples of the oral dissolvable film can be characterized and evaluated to ensure it possesses the desired aesthetic and performance characteristics, as well as any desired mechanical properties. From the regulatory perspectives, the oral dissolvable film can be characterized and evaluated consistent with relevant regulatory requirements and guidelines.

Organoleptic Evaluation

This in vivo taste evaluation is carried out on human volunteers. In vivo techniques analyze the taste and mouth feel of the product.

Stability

Stability can be carried out under accelerated stability conditions for an extended period of time. A typical program involves one or more (e.g., 1-8) storage conditions, with temperatures ranging from room temperature (19° C.) to elevated temperatures (e.g., 25-80° C.), and a relative humidity ranging from 10-75% relative humidity (RH).

Suitable accelerated stability conditions include, e.g., 25° C./60% RH, 30° C./65% RH, and 40° C./75% RH. The sample(s) can be stored under the selected stability conditions for an extended period of time (e.g., 3, 6, or 9 months). The drug product stability can then be obtained utilizing standard analytical procedures. For example, by dissolving the sample(s) in solvent, and measuring the qualitative and quantitative presence of active ingredient and/or impurities (e.g., degradants) present therein. This can typically be done utilizing standard analytical equipment (e.g., gas chromatography and mass spectrometry).

Tensile Strength

Tensile strength is defined as maximum stress applied at which the film breaks. Basically, this test is performed to measure the mechanical strength of films. It can be calculated from applied load at rupture divided by the strip cross-sectional area given in the equation below:

Tensile strength=(load at failure/strip thickness×strip width)×100

Moisture Uptake and Moisture Loss

Percent moisture loss is a parameter that determines the hygroscopicity of a film. Usually, this parameter is determined by first finding the initial weight of the film, afterward, putting this film in a desiccator for three days. The desiccator can contain a desiccant (e.g., calcium carbonate). After an extended period of time (24 hours, 1 day, 3 days, etc.), strips are taken out and weighed again. Moisture loss is determined by applying the following formula (Yellanki et al., 2011).

Percentage moisture loss=initial weight−final weight/ initial weight×100

Moisture uptake of a film is determined optionally sizing the film to a desired dimension (e.g., 2×2 cm$^2$). Afterward these strips are exposed to environment with a specified relative humidity (e.g., 60%, 75%, 90%, etc.) at room temperature for an extended period of time (e.g., up to 7 days). Moisture uptake is determined as percent weight gain of the strips (A. P. Gorle, S. G. Gattani; "Design and evaluation of polymeric ocular drug delivery system," Chem. Pharm. Bull., 57 (2009), pp. 914-919).

Content Uniformity

Contents of a film are determined by standard assay method specified for individual drug in different pharmacopoeia. This test can be performed on 20 samples using analytical techniques. The acceptance value of the test can be less than 15% in accordance with Japanese pharmacopoeia. According to USP27, the contents should range no more from 85% to 115% with the standard deviation of less than or equal to 6% (H. Chaudhary, S. Gauri, P. Rathee, V. Kumar; "Development and optimization of fast dissolving orodispersible films of granisetron HCl using Box-Behnken statistical design;" Bullet. FacultyPharm., 51 (2013), pp. 193-201). Content uniformity is worked out for estimating drug contents in individual film (B. Bhyan, S. Jangra, M. Kaur, H. Singh; "Orally fast dissolving films: innovations in formulation and technology;" Int. J. Pharm. Sci. Rev. Res., 9 (2011), pp. 9-15).

Kinetics or Erodibility

As used herein, the term "kinetics of erodibility" or "erosion kinetics" refers to the timing of the release of active ingredient from the oral dissolvable film (release profile), as well as, the timing of the erosion of the oral dissolvable film itself over time (lifespan or residence time of the oral film). As described herein, kinetics of erodibility are based on factors such as type and amount of ingredients in the oral dissolvable film, thickness and number of layers in the oral dissolvable film, and additives or excipients in the oral dissolvable film. In a case in which all the components of the oral dissolvable film are very water soluble, the kinetics of erodibility will closely parallel the solubility kinetics.

The residence time of the oral dissolvable films described herein depends on the erosion rate of the water erodible polymers used in the formulation and their respective concentrations. Upon application, water absorption softens the oral dissolvable film, thereby diminishing the foreign body sensation. As the composition rests on the mucosal surface, the oral dissolvable film erodes while delivery of the active ingredient occurs. The oral dissolvable film includes soluble polymers selected based on dissolution rates to achieve the desired residence time and release profile.

The erosion rate may be adjusted, for example, by mixing together components with different solubility characteristics or chemically different polymers, by using different molecular weight grades of the same polymer, or by using excipients or plasticizers of various lipophilic values or water solubility characteristics (including essentially insoluble components). These strategies might be employed alone or in combination in order to modify the erosion kinetics of the oral film.

Residence times may be adjusted over a wide range depending upon the desired timing of the delivery of the chosen active ingredient and the desired lifespan of the carrier. Generally, however, the residence time is modulated between about a few seconds to about a few hours. Preferably, when the oral dissolvable film is an oral thin film, the residence time for is adjusted from about 5 seconds to about 3 minutes. More preferably, the residence time is adjusted from about 10 seconds to about 2 minutes. In addition to providing drug delivery, once the oral dissolvable film is placed in the oral cavity, it can optionally adhere to the mucosal surface and provide protection to the treatment site, acting as an erodible bandage.

While not wishing to bound to a particular theory, it is believed that the adhesion properties of the oral dissolvable films described herein are the result of the entanglement of polymer chains and interactions with glycoproteins of the mucosal surface. The chemical nature of the bioadhesive polymers, including chain and side groups and crosslinking agents, generates interactions between the mucosal constituents and the polymer(s), such as physical entanglement, Van der Waals interactions, and hydrogen bonding.

The matrix of the orally dissolvable film generally falls into three main classes: (1) fast dissolution, (2) moderate dissolution, and (3) slow dissolution, each of which characterizes the time taken for the matrix of the film to dissolve. Fast dissolution matrixes generally dissolves in up to about 60 seconds, with it typically being less than about 20 seconds. Slow dissolution matrixes generally dissolve in more than 45 minutes, with it typically being more than about 60 minutes. Moderate dissolution matrixes tend to fall in between the fast dissolution and slow dissolution matrixes.

The active ingredient of the orally dissolvable film generally falls into three main classes: (1) fast dissolution, (2) moderate dissolution, and (3) slow dissolution, each of which characterizes the time taken for the active ingredient portion of the film to dissolve. Fast dissolution active ingredients generally dissolves in up to about 60 seconds, with it typically being less than about 30 seconds. Slow dissolution active ingredients generally dissolve in more than 30 minutes, with it typically being more than about 45 minutes. Moderate dissolution active ingredients tend to fall in between the fast dissolution and slow dissolution active ingredients.

Disintegration Time

There are no official guidelines available for determining disintegration time of orally disintegrating films (B. Bhyan, S. Jangra, M. Kaur, H. Singh; "Orally fast dissolving films: innovations in formulation and technology;" It. J. Pharm. Sci. Rev. Res., 9 (2011), pp. 9-15). However, disintegration apparatus mentioned in official pharmacopoeias can be used for determining the disintegration time of a film. Mostly, the USP disintegration apparatus is often used for this test. Normally, the disintegration time is the function of composition of film as it varies with the formulation. Provided herein below are several tests used to determine the disintegration times and dissolution times for oral thin films.

Disintegration and Dissolution Testing

Oral dissolvable films described herein are considered to be a dosage form that disintegrate rapidly in the oral cavity, with a short in vitro disintegration time (e.g., approximately up to about 60 seconds). Presently, neither United States Phamacopoeia (USP) nor the European Pharmacopoeia has defined a specific disintegration test for OTFs.

The results from the USP disintegration test <701> are believed to not provide a strong correlation with in vivo disintegration times in the mouth because the test uses a disintegration medium of about 900 mL of water and a vigorously oscillating apparatus, which provide conditions vastly different than those found in vivo of the oral cavity. See <701> Disintegration, in USP 29 (US Pharmacopieal (USP) Convention, Rockville, Md.) pp. 2670-2672. USP disintegration test <701> does not provide a good in vitro-in vivo correlation (IVIVC) for the disintegration time of an orally dissolvable film. The experimental conditions used do not simulate the wet tongue surface condition or the amount of saliva in the mouth at a given time. Therefore, it is desirable to employ simple alternative methods for evaluating the disintegration time of ODFs with these specific attributes:

Testing conditions closely simulate the physiological conditions in the mouth, specifically the wet tongue surface and the volume of saliva Good reproducibility by various operators Reasonable IVIVC Suitable as a quick screening tool for discerning if a dosage form should be labeled as an OTF.

Currently there is no USP in vitro method for evaluating disintegration time for OTFs, which represents in vivo disintegration time in the mouth. Therefore, in the absence of any such USP in vitro methods, modified forms of the USP disintegration test <701> can be developed and employed.

The proposed test methods provided below require minimum equipment so that they allow review scientists to evaluate, in an laboratory setting, the disintegration and/or dissolution of ODFs submitted for FDA approval. They can also serve as a quick screening tool for review scientists to decide whether a dosage form is appropriately labeled as an ODF.

Selection of an appropriate disintegration or dissolution test can vary, depending upon, e.g., the specific product, the rate of dissolution or disintegration of the product, etc. For example, especially with controlled substances (drug whose manufacture, possession, or use is regulated by the Drug Enforcement Administration of the U.S. federal government) Disintegration Test Method 18-9-22-Z below would likely not be used, as it is an in vivo test conducted on a population of volunteers. As such, several alternative and viable tests are provided below. The practitioner may elect to test the product employing a single test provided below. Alternatively, the practitioner may elect to test the product employing multiple tests. In doing so, the practitioner can determine which are suitable and appropriate. Additionally, the practitioner can obtain a statistical mean, median, and/or mode employing one or more of the multiple tests provided below.

Disintegration Test Method 18-9-22-A

Apparatus

The assembly consists of the following: 200 ml glass beaker and overhead stirrer with the capability of stirring 100 rpm.

Procedure

1. Fill the 200 ml glass beaker with 100 ml of solvent (e.g., water, saliva, gastric fluid).
2. Heat the temperature of the solvent to 37° C.
3. Set the overhead stirrer to 100 rpm but do not turn on the mixer.
4. Place the beaker under the overhead stirrer with mixer head submerged in the solvent.
5. Measure the thickness of the ODF sample (n>10; average and SD)
6. Place the sample on the inside wall of the beaker. Make sure the sample is fully submerged in the solvent.
7. Turn on the overhead stirrer.

8. Record the time it takes for the thin film sample to completely disintegrate. Begin the timer when the overhead stirrer is turned on.
9. Repeat the process 2 more times and calculate the average time.

Disintegration Test Method 18-9-22-B

Apparatus

Required equipment: Micropipette

Procedure

1. Heat the solvent (e.g., water, saliva, gastric fluid) to 37° C.
2. Measure the thickness of the ODF sample (n>10, average and SD)
3. Place the sample on a clean flat surface.
4. Pipette 150 μl of the solvent onto the center of the sample.
5. Record the time it takes for the drop of solvent to penetrate completely through the sample. Begin the timer when the drop is placed on the sample.
6. Repeat the process 2 more times and calculate the average time.

Disintegration Test Method 18-9-22-C

Apparatus

Required equipment: Petri dish

Procedure

1. Heat the solvent (distilled water or any applicable media e.g. saliva, gastric fluid) to 37° C.
2. Measure the thickness of the oral thin film sample (n>10, average and SD)
3. Place 2 ml of the solvent into the petri dish.
4. Place the thin film sample on the surface of the solvent.
5. Record the time it takes for the sample to break into small particles. Begin when the sample is placed into the petri dish.
6. Repeat the process 2 more times and calculate average time.

Modified Dissolution Test Method 18-9-22-D

Apparatus

The assembly consists of the following: HPLC, 200 ml glass beaker, overhead stirrer with the capability of stirring 100 rpm, HPLC vials, pipettes, timer, filters, syringe.

Procedure

1. Fill the 200 ml glass beaker with 100 ml of dissolution media (dependent on active and development studies).
2. Heat the temperature of the solvent to 37° C.
3. Set the overhead stirrer to 100 rpm but do not turn on the mixer.
4. Place the beaker under the overhead stirrer with mixer head submerged in the solvent.
5. Measure the thickness and weight of the ODF sample (n>10, average and SD).
6. Place the sample on the inside wall of the beaker so it adheres to the wall. Make sure the sample is fully submerged in the solvent.
7. Turn on the overhead stirrer.
8. Take sample aliquots at the following timepoints or as pre-determined and ensure volume is replaced with fresh media:
    a. 1 minutes
    b. 5 minutes
    c. 10 minutes
    d. 30 minutes
    e. 60 minutes
    f. 120 minutes
    g. 180 minutes If need, continue as defined by product profile and development plan.

9. Replace media solution with fresh media each time sample is taken with the same amount of media that was withdrawn.
10. If needed, filter sample using 0.45 μm filter and syringe before analysis.
11. Quantify the amount of active at each timepoint using the HPLC.
12. Graph the Concentration of the Active vs. Time or % Release over time. Report the final cumulative drug release.
13. Dissolution rate can be calculated by plotting % cumulative drug release vs square root of time.

Disintegration Test Method 18-9-22-X

A quick and simple modified test was designed to help regulatory review scientists in evaluating the ODFs. Using a disposable syringe, 1 mL of water is delivered directly onto a film placed on a flat surface. Completeness of disintegration of the film is checked by the manual palpation of the film at the end of a predetermined period of time (e.g., 90 s, 60 s, or 30 s).

Disintegration Test Method 18-9-22-Y

A quick and simple modified test was designed to help regulatory review scientists in evaluating the ODFs. A given volume of water is used as a medium to mimic physiological conditions. A 10-cm diameter Petri dish is filled with 10 mL of water containing eosin, a water soluble dye. A 10-cm diameter circular tissue paper is placed in the Petri dish. The ODF is carefully placed in the center of the dish and the time for the film to completely disintegrate is noted as the disintegration time.

Disintegration Test Method 18-9-22-Z

An in vivo test of sample ODF is conducted on a population of volunteers. Each volunteer receives a sample ODF. Each volunteer is asked to place a sample ODF in their oral cavity (e.g., on the tongue) and to indicate when the film completely disintegrates. The time for disintegration is measured by using a stopwatch. The participants are instructed what they can or cannot do while measuring the time to mimic as close as possible the intended intake by the target patient (e.g., buccal ODF should not be interrupted with tongue movement). Immediately after the film disintegrates completely, the stopwatch is stopped and the time recorded.

Specific Ranges, Values, and Embodiments

The specific embodiments describing the ranges and values provided below are for illustration purposes only, and do not otherwise limit the scope of the disclosed subject matter, as defined by the claims.

In specific embodiments, the orally disintegrating film matrix is formulated as an oral dissolvable film.

In specific embodiments, the orally disintegrating film matrix is formulated as an oral thin film.

In specific embodiments, the orally disintegrating film matrix is an oral dissolvable film.

In specific embodiments, the orally disintegrating film matrix is an oral thin film.

In specific embodiments, the orally disintegrating film matrix is formulated as a film roll.

In specific embodiments, the orally disintegrating film matrix is formulated as a bulk roll.

In specific embodiments, the orally disintegrating film matrix further includes residual solvent.

In specific embodiments, the orally disintegrating film matrix further includes residual solvent containing bound water and/or unbound water.

In specific embodiments, the orally disintegrating film matrix further includes residual water in up to 8 wt. %.

In specific embodiments, the orally disintegrating film matrix further includes residual water in up to 7.5 wt. %.

In specific embodiments, the orally disintegrating film matrix further includes residual water in up to 7 wt. %.

In specific embodiments, the orally disintegrating film matrix further includes residual water in up to 6.5 wt. %.

In specific embodiments, the orally disintegrating film matrix further includes residual water in up to 6 wt. %.

In specific embodiments, the orally disintegrating film matrix further includes residual water in up to 5.5 wt. %.

In specific embodiments, the orally disintegrating film matrix further includes residual water in up to 5 wt. %.

In specific embodiments, the orally disintegrating film matrix further includes residual water in up to 4.5 wt. %.

In specific embodiments, the orally disintegrating film matrix further includes residual water in up to 4 wt. %.

In specific embodiments, the orally disintegrating film matrix further includes residual water in up to 3.5 wt. %.

In specific embodiments, the orally disintegrating film matrix further includes residual water in 3-8 wt. %.

In specific embodiments, the orally disintegrating film matrix further includes residual water in 3-7.5 wt. %.

In specific embodiments, the orally disintegrating film matrix further includes residual water in 3-7 wt. %.

In specific embodiments, the orally disintegrating film matrix further includes residual water in 3-6.5 wt. %.

In specific embodiments, the orally disintegrating film matrix further includes residual water in 3-6 wt. %.

In specific embodiments, the orally disintegrating film matrix further includes residual water in 3-5.5 wt. %.

In specific embodiments, the orally disintegrating film matrix further includes residual water in 3-5 wt. %.

In specific embodiments, the orally disintegrating film matrix further includes residual water in 3-4.5 wt. %.

In specific embodiments, the orally disintegrating film matrix further includes residual water in 3-4 wt. %.

In specific embodiments, the orally disintegrating film matrix further includes residual water in 3.5-8 wt. %.

In specific embodiments, the orally disintegrating film matrix further includes residual water in 3.5-7.5 wt. %.

In specific embodiments, the orally disintegrating film matrix further includes residual water in 3.5-7 wt. %.

In specific embodiments, the orally disintegrating film matrix further includes residual water in 3.5-6.5 wt. %.

In specific embodiments, the orally disintegrating film matrix further includes residual water in 3.5-6 wt. %.

In specific embodiments, the orally disintegrating film matrix further includes residual water in 3.5-5.5 wt. %.

In specific embodiments, the orally disintegrating film matrix further includes residual water in 3.5-5 wt. %.

In specific embodiments, the orally disintegrating film matrix further includes residual water in 3.5-4.5 wt. %.

In specific embodiments, the orally disintegrating film matrix further includes residual water in 3.5-4 wt. %.

In specific embodiments, the orally disintegrating film matrix has a moisture content of less than 8 wt. %.

In specific embodiments, the orally disintegrating film matrix has a moisture content of less than 7.5 wt. %.

In specific embodiments, the orally disintegrating film matrix has a moisture content of less than 7 wt. %.

In specific embodiments, the orally disintegrating film matrix has a moisture content of less than 6.5 wt. %.

In specific embodiments, the orally disintegrating film matrix has a moisture content of less than 6 wt. %.

In specific embodiments, the orally disintegrating film matrix has a moisture content of less than 5.5 wt. %.

In specific embodiments, the orally disintegrating film matrix has a moisture content of less than 5 wt. %.

In specific embodiments, the orally disintegrating film matrix has a moisture content of less than 4.5 wt. %.

In specific embodiments, the orally disintegrating film matrix has a moisture content of less than 4 wt. %.

In specific embodiments, the orally disintegrating film matrix has a moisture content of 3-8 wt. %.

In specific embodiments, the orally disintegrating film matrix has a moisture content of 3-7.5 wt. %.

In specific embodiments, the orally disintegrating film matrix has a moisture content of 3-7 wt. %.

In specific embodiments, the orally disintegrating film matrix has a moisture content of 3-6.5 wt. %.

In specific embodiments, the orally disintegrating film matrix has a moisture content of 3-6 wt. %.

In specific embodiments, the orally disintegrating film matrix has a moisture content of 3-5.5 wt. %.

In specific embodiments, the orally disintegrating film matrix has a moisture content of 3-5 wt. %.

In specific embodiments, the orally disintegrating film matrix has a moisture content of 3-4.5 wt. %.

In specific embodiments, the orally disintegrating film matrix has a moisture content of 3-4 wt. %.

In specific embodiments, the orally disintegrating film matrix has a moisture content of 3.5-8 wt. %.

In specific embodiments, the orally disintegrating film matrix has a moisture content of 3.5-7.5 wt. %.

In specific embodiments, the orally disintegrating film matrix has a moisture content of 3.5-7 wt. %.

In specific embodiments, the orally disintegrating film matrix has a moisture content of 3.5-6.5 wt. %.

In specific embodiments, the orally disintegrating film matrix has a moisture content of 3.5-6 wt. %.

In specific embodiments, the orally disintegrating film matrix has a moisture content of 3.5-5.5 wt. %.

In specific embodiments, the orally disintegrating film matrix has a moisture content of 3.5-5 wt. %.

In specific embodiments, the orally disintegrating film matrix has a moisture content of 3.5-4.5 wt. %.

In specific embodiments, the orally disintegrating film matrix has a moisture content of 3.5-4 wt. %.

In specific embodiments, the orally disintegrating film matrix, upon contact with the oral cavity, disintegrates within 60 seconds.

In specific embodiments, the orally disintegrating film matrix, upon contact with the oral cavity, disintegrates within 45 seconds.

In specific embodiments, the orally disintegrating film matrix, upon contact with the oral cavity, disintegrates within 30 seconds.

In specific embodiments, the orally disintegrating film matrix, upon contact with the oral cavity, disintegrates within 20 seconds.

In specific embodiments, the orally disintegrating film matrix, upon contact with the oral cavity, disintegrates within 15 seconds.

In specific embodiments, the orally disintegrating film matrix, upon contact with the oral cavity, disintegrates within 10 seconds.

In specific embodiments, the orally disintegrating film matrix includes a first active ingredient present when the orally disintegrating film matrix is formed.

In specific embodiments, the orally disintegrating film matrix includes a second active ingredient added after the orally disintegrating film matrix is formed.

In specific embodiments, the orally disintegrating film matrix includes a first active ingredient present when the orally disintegrating film matrix is formed, and the orally disintegrating film matrix includes a second active ingredient added after the orally disintegrating film matrix is formed.

In specific embodiments, the active ingredient is an active pharmaceutical ingredient (API), nutraceutical, dietary supplement, or vitamin.

In specific embodiments, the active ingredient is an active pharmaceutical ingredient (API).

In specific embodiments, the active ingredient is a nutraceutical.

In specific embodiments, the active ingredient is a dietary supplement.

In specific embodiments, the active ingredient is a vitamin.

In specific embodiments, the active ingredient is a cannabinoid.

In specific embodiments, the active ingredient is a terpene.

In specific embodiments, the active ingredient is at least one of moisture sensitive, heat sensitive, pH sensitive, oxygen sensitive, light (UV) sensitive, and has an unpleasant taste or odor.

In specific embodiments, the active ingredient is moisture sensitive.

In specific embodiments, the active ingredient is heat sensitive.

In specific embodiments, the active ingredient is pH sensitive.

In specific embodiments, the active ingredient is oxygen sensitive.

In specific embodiments, the active ingredient is light (UV) sensitive.

In specific embodiments, the active ingredient has an unpleasant taste or odor.

In specific embodiments, the active ingredient is water-insoluble (e.g., solubility of less than 1 mg/10 ml water). In further specific embodiments, the active ingredient is water-insoluble such that it has a solubility, in 10 ml water, of less than 0.5 mg. In further specific embodiments, the active ingredient is water-insoluble such that it has a solubility, in 10 ml water, of less than 0.25 mg. In further specific embodiments, the active ingredient is water-insoluble such that it has a solubility, in 10 ml water, of less than 0.1 mg. In further specific embodiments, the active ingredient is water-insoluble such that it has a solubility, in 10 ml water, of less than 0.05 mg.

In specific embodiments, the active ingredient is present in a small quantity (e.g., present in less than 1 mg per unit dosage form). In further specific embodiments, the active ingredient is present in less than 0.75 mg per unit dosage form. In further specific embodiments, the active ingredient is present in less than 0.5 mg per unit dosage form. In further specific embodiments, the active ingredient is present in less than 0.25 mg per unit dosage form. In further specific embodiments, the active ingredient is present in less than 0.1 mg per unit dosage form. In further specific embodiments, the active ingredient is present in less than 0.075 mg per unit dosage form. In further specific embodiments, the active ingredient is present in less than 0.05 mg per unit dosage form. In further specific embodiments, the active ingredient is present in less than 0.025 mg per unit dosage form. In further specific embodiments, the active ingredient is present in less than 0.01 mg per unit dosage form.

In specific embodiments, the moisture sensitive active ingredient includes one or more of desmopressin (DDAVP) (D-amino D-arginine vasopressin); dronabinol ((−)-trans-$\Delta^9$-tetrahydrocannabinol); aspirin (acetylsalicylic acid); penicillin (PCN); dipyridamole; vorapaxar; procaine; atorvastatin; azithromycin; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; methyldopamine; naproxen; acetaminophen; erythromycin; bupropion; rifapentine; penicillamine; mexiletine; verapamil; diltiazem; ibuprofen; cyclosporine; saquinavir; morphine; sertraline; cetirizine; N-[[2-methoxy-5-(I-methyl)phenyl]methyl]-2-(diphenylmethyl)-1-azabicylco[2.2.2]octan-3-amine; adrenaline; amiodarone hydrochloride; atropine sulphate; diazepam; ephedrine; frusemide; haloperidol; lignocaine; metoclopramide; noradrenaline; omeprazole; ondansetron; phenytoin; vercuronium; acyclovir; amoxicillin; cefotetan; cefotaxime; metronidazole; cefuroxime; flucloxacillin; bupivacaine; cilazapril; amlodipine; felodipine; fesoterodine; isradipine; nifedipine; nimodipine; nisoldipine; cyclosporine; saquinavir; itraconazole; and ketoconazole.

In specific embodiments, the oxygen sensitive active ingredient includes one or more of dronabinol ((−)-trans-$\Delta^9$-tetrahydrocannabinol); epinephrine (also known as adrenalin or adrenaline); dopamine (3,4-dihydroxyphenethylamine); chlorpromazine (CPZ); captopril; azithromycin; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; methyldopamine; naproxen; acetaminophen; erythromycin; bupropion; rifapentine; penicillamine; mexiletine; verapamil; diltiazem; ibuprofen; cyclosporine; saquinavir; morphine; sertraline; cetirizine; N-[[2-methoxy-5-(l-methyl)phenyl]methyl]-2-(diphenylmethyl)-1-azabicylco[2.2.2]octan-3-amine; adrenaline; amiodarone hydrochloride; atropine sulphate; diazepam; ephedrine; frusemide; haloperidol; lignocaine; metoclopramide; noradrenaline; omeprazole; ondansetron; phenytoin; vercuronium; acyclovir; amoxicillin; cefotetan; cefotaxime; metronidazole; cefuroxime; flucloxacillin; bupivacaine; methylphenidate; fesoterodine fumarate; morphine; hydromorphone; promethazine; dopamine; epinephrine; norepinephrine; esterified estrogen; ephedrine; pseudoephedrine; acetaminophen; ibuprofen; danofloxacin; erythromycin; penicillin; cyclosporine; methyldopate; cetirizine; diltiazem; verapamil; mexiletine; chlorothiazide; carbamazepine; selegiline; oxybutynin; vitamin A; vitamin B; vitamin C; L-cysteine; L-tryptophan; morphine; hydromorphone; promethazine; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; methyldopa; naproxen; acetaminophen; erythromycin; bupropion; rifapentine; penicillamine; mexiletine; verapamil; diltiazem; ibuprofen; cyclosporine; saquinavir; morphine; sertraline; cetirizine; and N-[[2-methoxy-5-(1-methyl)phenyl]methyl]-2-(diphenylmethyl)-1-azabicylco[2.2.2]octan-3-amine.

In specific embodiments, the pH sensitive active ingredient includes one or more of desmopressin (DDAVP) (D-amino D-arginine vasopressin); vitamin D3 (cholecalciferol); omeprazole; and esomeprazole.

In specific embodiments, the heat sensitive active ingredient includes one or more of dronabinol ((−)-trans-$\Delta^9$-tetrahydrocannabinol); aspirin (acetylsalicylic acid); vitamin D3 (cholecalciferol); diazepam; epinephrine (also known as adrenalin or adrenaline); omeprazole; esomeprazole; and diazepam.

In specific embodiments, the light (UV) sensitive active ingredient includes one or more of penicillin (PCN); diazepam; tretinoin; isotretinoin; naproxen; erythromycin; diazepam; haloperidol; acyclovir; amlodipine; isradipine; nifedipine; promethazine; norepinephrine; promethazine; tretinoin; naproxen; digoxin; nitroglycerin; aminophylline; amphotericin B; chlorpheniramine maleate; chlorpromazine HCl; cisplatin; dacarbazine; diazoxide; diphenhydramine; dopamine hydrochloride; doxycycline hyclate; droperidol; epinephrine hydrochloride; fluorouracil; folic acid; furosemide; hydrocortisone; isoproterenol; levarterenol bitartrate; menadiol sodium diphosphate; methadone; morphine sulphate; naloxone; neostigmine methylsulfate; nitroprusside solution; phenylephrine hydrochloride; phytonadione; prochlorperazine edisylate; propranolol hydrochloride; streptomycin sulphate; sulfisoxazole diolamine; terbutaline; testosterone cypionate; triflupromazine hydrochloride; vinblastine; vincristine sulphate; vitamin B complex; dextroamphetamine; ciprofloxacin; clarithromycin; griseofulvin; itraconazole; ketoconazole; terbinafine; tetracycline hydrochloride; 1,4-dihydropyridines; 4-nerolidylcatechol; avobenzone; barnidipine; butyl methoxydibenzoylmethane; doxorubicin; fluoroquinolones; melatonin; naltrexone; cephalosporins; resveratrol; sericin; 3-hydroxyflavone; 4-methylbenzylidene camphor; 5-hydroxyflavones; antazoline; xylometazoline; nafazoline; ascorbic acid; carvedilol; cilnidipine; diclofenac; diflunisal; doxycycline; lansoprazole; manidipine; methotrexate; nicardipine; ofloxacin; oxolinic acid; phenylpropanoids; quercetin; ranitidine; rhein; sulfanilamide; and triprolidine.

In specific embodiments, the active ingredient having an unpleasant odor or taste includes one or more of aspirin (acetylsalicylic acid); penicillin (PCN); dipyridamole; procaine; diazepam; pseudoephedrine; oxybutynin; erythromycin; bupropion; ibuprofen; diazepam; ondansetron; acetaminophen; ibuprofen; alprazolam; chlorpheniramine maleate; diphenhydramine; ciprofloxacin; clarithromycin; diclofenac; ofloxacin; ranitidine; valerian extracts; isometheptene; bucillamine; azilsartan medoxomil, olmesartan medoxomil; benzalkonium chloride; diacetyl/2,3-butanedione; zinc acetate dihydrate; phenylpropanolamine hydrochloride; famotidine; pogostemi herba; guaifenesin; thymol; eucalyptus oil; benzethonium chloride; theophylline; anticholesterolemic saponins; cimetidine; gabapentin; isoprothiolane; carbetapentane citrate; noscapine hydrochloride; quinine; L-leucine; iso-leucine; papaverine; talampicillin hydrochloride; indeloxazine hydrochloride; pinaverium bromide; propantheline bromide; triprolidine hydrochloride; dimenhydrinate; enoxacin; sparfloxacin; famotidine; amoxycillin trihydrate; morphine hydrochloride; amiprilose hydrochloride; terfenadine; beclamide; cetraxate; bifemelane hydrochloride; cefuroxime axetil; pirenzepine; nicorandil; levofloxacin; gymnema sylvestre; buflomedil; orbifloxacin; chloroquine phosphate; famotidine; etoricoxib; pivoxil sulbactam; cetirizine dihydrochloride; cefpodoxime proxetil; desloratadine; dextromethorphan; amobarbital; sildenafil citrate; granisetron hydrochloride; levofloxacin; clopidogrel sulfate; telithromycin; pristinamycin; dihydrocodeine phosphate; potassium guaiacol sulfonate; fluoxetine; praziquantel; epsiprantel; risperidone; roxithromycin; bromhexine; paracetamol; pioglitazone; donepezil chloride; and sildenafil.

In specific embodiments, the water insoluble active ingredient includes one or more of dronabinol ((−)-trans-$\Delta^9$-tetrahydrocannabinol); diazepam; tretinoin; isotretinoin; carbamazepine; naproxen; ibuprofen; saquinavir; diazepam; nimodipine; acetaminophen; carbamazepine; carbamazepine; naproxen; ibuprofen; cyclosporine; saquinavir; estradiol; dexamethasone; dutasteride; doxercalciferol; calcitriol; tacrolimus; lorazepam; repaglinide; sirolimus; amphotericin B; griseofulvin; itraconazole; tetracycline hydrochloride; aprepitant; fenofibrate; paliperidone; aripiprazole lauroxil; progesterone; spironolactone; diosmin; celecoxib; halofantrine hydrochloride; ritonavir; meloxicam; nimesulide; danazol; glibenclamide; teniposide; propanidid; lopinavir; nabilone; etravirine; aprepitant; megestrol; nystatin; etomidate; flurbiprofen; propofol; clofazimine; paricalcitol; and tipranavir.

In specific embodiments, the active ingredient present in a small quantity includes one or more of benztropine mesylate; colchicine; desmopressin acetate; ethinyl estradiol; estradiol; esterified estrogens; estropipate; levothyroxine sodium; everolimus; anagrelide hydrochloride; dexamethasone; clonazepam; diethylstilbestrol; digoxin; quinestrol; palonosetron hydrochloride; clonidine hydrochloride; bromocriptine mesylate; conjugated synthetic b estrogens; entecavir; liotrix (t4;t3); dutasteride; rescinnamine; haloperidol; dofetilide; doxercalciferol; tamsulosin hydrochloride; triazolam; deserpidine; reserpine; zalcitabine; ergoloid mesylates; calcitriol; calcifediol; fludrocortisone acetate; atropine sulfate; levonorgestrel; norethindrone acetate; estradiol acetate; tacrolimus; liothyronine sodium; misoprostol; diphenoxylate hydrochloride; cabergoline; fingolimod hydrochloride; topotecan hydrochloride; dutasteride; tamsulosin hydrochloride; lorazepam; cyanocobalamin co-57; cyanocobalamin co-60; sodium iodide i-131; talazoparib tosylate; alosetron hydrochloride; lofexidine hydrochloride; trametinib dimethyl sulfoxide; methylergonovine maleate; pramipexole dihydrochloride; metolazone; nitroglycerin; buprenorphine hydrochloride; naloxone hydrochloride; fentanyl citrate; norgestrel; pergolide mesylate; fluphenazine hydrochloride; repaglinide; sirolimus; rasagiline mesylate; ropinirole hydrochloride; brexpiprazole; naldemedine tosylate; selexipag; norethindrone; sufentanil citrate; alprazolam; clonidine; treprostinil diolamine; acetyldigitoxin; riociguat; drospirenone; cerivastatin sodium; bumetanide; betamethasone; varenicline tartrate; and fentanyl.

In specific embodiments, the active ingredient is a cannabinoid and is selected from the group consisting of THC (tetrahydrocannabinol), THCA (tetrahydrocannabinolic acid), CBD (cannabidiol), CBDA (cannabidiolic Acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), and mixtures thereof.

In specific embodiments, the active ingredient is a cannabinoid obtained as a distillate from cannabis.

In specific embodiments, the active ingredient is a cannabinoid obtained as an extract from cannabis.

In specific embodiments, the active ingredient is a cannabinoid obtained as a resin from cannabis.

In specific embodiments, the active ingredient is a cannabinoid isolate obtained from cannabis.

In specific embodiments, the active ingredient is a cannabinoid obtained from *Cannabis indica, Cannabis ruderalis,* or *Cannabis sativa.*

In specific embodiments, the active ingredient is cannabinoid present as an oil from cannabis.

In specific embodiments, the active ingredient is a cannabinoid present as hempseed oil.

In specific embodiments, the active ingredient is a cannabinoid that is synthetically prepared.

In specific embodiments, the active ingredient is at least one of THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

In specific embodiments, the active ingredient is THC (tetrahydrocannabinol).

In specific embodiments, the active ingredient is CBD (cannabidiol).

In specific embodiments, the active ingredient is a terpene.

In specific embodiments, the active ingredient is a terpene that is a sesquiterpene.

In specific embodiments, the active ingredient is a terpene obtained as a distillate from plant matter.

In specific embodiments, the active ingredient is a terpene obtained as an extract from plant matter.

In specific embodiments, the active ingredient is a terpene obtained as a resin from plant matter.

In specific embodiments, the active ingredient is a terpene obtained from *Cannabis sativa, Syzygium aromaticum* (cloves), rosemary, or hops.

In specific embodiments, the active ingredient is a terpene that is synthetically prepared.

In specific embodiments, the active ingredient is Beta-Caryophyllene.

In specific embodiments, the first active ingredient is moisture sensitive.

In specific embodiments, the first active ingredient is oxygen sensitive.

In specific embodiments, the first active ingredient is pH sensitive.

In specific embodiments, the first active ingredient is heat sensitive.

In specific embodiments, the first active ingredient is present in a small quantity.

In specific embodiments, the first active ingredient is a cannabinoid.

In specific embodiments, the first active ingredient is a terpene.

In specific embodiments, the second active ingredient is moisture sensitive.

In specific embodiments, the second active ingredient is oxygen sensitive.

In specific embodiments, the second active ingredient is pH sensitive.

In specific embodiments, the second active ingredient is heat sensitive.

In specific embodiments, the second active ingredient is present in a small quantity.

In specific embodiments, the second active ingredient is a cannabinoid.

In specific embodiments, the second active ingredient is a terpene.

In specific embodiments, the second active ingredient is desmopressin (D-amino D-arginine vasopressin).

In specific embodiments, the first active ingredient is present (i.e., the orally disintegrating film matrix includes the first active ingredient) and the second active ingredient is absent (i.e., the orally disintegrating film matrix does not includes the second active ingredient).

In specific embodiments, the first active ingredient is present (i.e., the orally disintegrating film matrix includes the first active ingredient) and the second active ingredient is present (i.e., the orally disintegrating film matrix includes the second active ingredient).

In specific embodiments, the first active ingredient is absent (i.e., the orally disintegrating film matrix does not include the first active ingredient) and the second active ingredient is present (i.e., the orally disintegrating film matrix includes the second active ingredient).

In specific embodiments, the first active ingredient is absent (i.e., the orally disintegrating film matrix does not include the first active ingredient) and the second active ingredient is absent (i.e., the orally disintegrating film matrix does not include the second active ingredient).

In specific embodiments, the first and second active ingredients are the same.

In specific embodiments, the first and second active ingredients are different.

In specific embodiments, the first active ingredient is present in the orally disintegrating film matrix in 0.01-100 mg.

In specific embodiments, the first active ingredient is present in the orally disintegrating film matrix in 0.1-100 mg.

In specific embodiments, the first active ingredient is present in the orally disintegrating film matrix in 5-100 mg.

In specific embodiments, the first active ingredient is present in the orally disintegrating film matrix in 5-50 mg.

In specific embodiments, the first active ingredient is present in the orally disintegrating film matrix in 50±20 mg.

In specific embodiments, the first active ingredient is present in the orally disintegrating film matrix in 50±10 mg.

In specific embodiments, the first active ingredient is present in the orally disintegrating film matrix in 25±20 mg.

In specific embodiments, the first active ingredient is present in the orally disintegrating film matrix in 25±10 mg.

In specific embodiments, the first active ingredient is present in the orally disintegrating film matrix in 1-30 wt. %.

In specific embodiments, the first active ingredient is present in the orally disintegrating film matrix in 2-20 wt. %.

In specific embodiments, the first active ingredient is present in the orally disintegrating film matrix in 10±5 wt. %.

In specific embodiments, the second active ingredient is present in the orally disintegrating film matrix in 0.01-1 mg.

In specific embodiments, the second active ingredient is present in the orally disintegrating film matrix in 0.01-0.75 mg.

In specific embodiments, the second active ingredient is present in the orally disintegrating film matrix in 0.01-0.5 mg.

In specific embodiments, the second active ingredient is present in the orally disintegrating film matrix in 0.01-0.25 mg.

In specific embodiments, the second active ingredient is present in the orally disintegrating film matrix in 0.05-1 mg.

In specific embodiments, the second active ingredient is present in the orally disintegrating film matrix in 0.05-0.75 mg.

In specific embodiments, the second active ingredient is present in the orally disintegrating film matrix in 0.05-0.5 mg.

In specific embodiments, the second active ingredient is present in the orally disintegrating film matrix in 0.05-0.25 mg.

In specific embodiments, the second active ingredient is present in the orally disintegrating film matrix in 0.3±0.25 mg.

In specific embodiments, the second active ingredient is present in the orally disintegrating film matrix in 0.3±0.1 mg.

In specific embodiments, the second active ingredient is present in the orally disintegrating film matrix in 0.1-3 wt. %.

In specific embodiments, the second active ingredient is present in the orally disintegrating film matrix in 0.2-2 wt. %.

In specific embodiments, the second active ingredient is present in the orally disintegrating film matrix in 1±0.75 wt. %.

In specific embodiments, the second active ingredient is present in the orally disintegrating film matrix in 1±0.5 wt. %.

In specific embodiments, the second active ingredient is present in the orally disintegrating film matrix in 1±0.25 wt. %.

In specific embodiments, the second active ingredient is present in the orally disintegrating film matrix in 0.4±0.3 wt. %.

In specific embodiments, the second active ingredient is present in the orally disintegrating film matrix in 0.4±0.2 wt. %.

In specific embodiments, the second active ingredient is present in the orally disintegrating film matrix in 0.4±0.1 wt. %.

In specific embodiments, the first active ingredient is CBD and is present in the orally disintegrating film matrix in up to 50 mg.

In specific embodiments, the first active ingredient is CBD and is present in the orally disintegrating film matrix in up to 25 mg.

In specific embodiments, the first active ingredient is CBD and is present in the orally disintegrating film matrix in 15±10 mg.

In specific embodiments, the first active ingredient is CBD and is present in the orally disintegrating film matrix in 15±5 mg.

In specific embodiments, the first active ingredient is CBD and is present in the orally disintegrating film matrix in 15±1 mg.

In specific embodiments, the second active ingredient is a schedule I, II, III, or IV drug substance.

In specific embodiments, the second active ingredient is a narcotic (e.g., Dextropropoxyphene or Tramadol).

In specific embodiments, the second active ingredient is a depressant (e.g., Fospropofol, Barbital, Suvorexant, Methylphenobarbital (mephobarbital), Methohexital, Phenobarbital, Chloral betaine, Chloral hydrate, Dichloraphenazone, Ethchlorvynol, Ethinamate, Paraldehyde, Petrichloral, Alfaxalone, Clonazepam, Chlordiazepoxide, Bromazepam, Camazepam, Clobazam, Clotiazepam, Cloxazolam, Delorazepam, Estazolam, Ethyl loflazepate, Fludiazepam, Halazepam, Flunitrazepam, Prazepam, Diazepam, Flurazepam, Clorazepate, Haloxazolam, Ketazolam, Loprazolam, Lormetazepam, Zaleplon, Zolpidem, Zopiclone, Mebutamate, Meprobamate, Nitrazepam, Oxazepam, Medazepam, Nimetazepam, Nordiazepam, Oxazolam, Quazepam, Alprazolam, Pinazepam, Midazolam, Lorazepam, Tetrazepam, Triazolam, Temazepam, or Carisoprodol).

In specific embodiments, the second active ingredient is Fenfluramine, Lorcaserin, Pentazocine, Butorphanol, or Eluxadoline.

In specific embodiments, the second active ingredient is a stimulant (e.g., Cathine, Diethylpropion, Fencamfamin, Fenproporex, Mazindol, Mefenorex, Modafinil and enantiopure armodafinil, Pemoline, Phentermine, Pipradrol, Sibutramine, or SPA/(−)-1-dimethylamino-1,2-diphenylethane.

In specific embodiments, the orally disintegrating film matrix has a mass of at least 50 mg.

In specific embodiments, the orally disintegrating film matrix has a mass of up to 350 mg.

In specific embodiments, the orally disintegrating film matrix has a mass of 200±50 mg.

In specific embodiments, the orally disintegrating film matrix has a mass of 200±30 mg.

In specific embodiments, the orally disintegrating film matrix has a mass of 200±20 mg.

In specific embodiments, the orally disintegrating film matrix has a thickness of less than 0.180 mm.

In specific embodiments, the orally disintegrating film matrix has a thickness of less than 0.160 mm.

In specific embodiments, the orally disintegrating film matrix has a thickness of less than 0.150 mm.

In specific embodiments, the orally disintegrating film matrix has a thickness of less than 0.130 mm.

In specific embodiments, the orally disintegrating film matrix has a thickness of less than 0.125 mm.

In specific embodiments, the orally disintegrating film matrix has a thickness of less than 0.120 mm.

In specific embodiments, the orally disintegrating film matrix is non-hygroscopic.

In specific embodiments, the orally disintegrating film matrix is non-hygroscopic, such that at a glass climatic chamber at 25° C. and at a relative humidity of 60%, the final water content on adsorption after 24 hours is less than 12 wt. %.

In specific embodiments, the orally disintegrating film matrix is non-hygroscopic, such that at a glass climatic chamber at 25° C. and at a relative humidity of 60%, the final water content on adsorption after 24 hours is less than 10 wt. %.

In specific embodiments, the orally disintegrating film matrix is non-hygroscopic, such that at a glass climatic chamber at 25° C. and at a relative humidity of 60%, the final water content on adsorption after 24 hours is less than 8 wt. %.

In specific embodiments, the orally disintegrating film matrix is non-hygroscopic, such that at a glass climatic chamber at 25° C. and at a relative humidity of 60%, the final water content on adsorption after 24 hours is less than 6 wt. %.

In specific embodiments, the orally disintegrating film matrix is non-hygroscopic, such that at a glass climatic chamber at 25° C. and at a relative humidity of 60%, the final water content on adsorption after 24 hours is less than 5 wt. %.

In specific embodiments, the orally disintegrating film matrix has a content uniformity, such that among two or more samples, the amount of first active ingredient ranges from 90% to 110%, with the standard deviation of less than or equal to 6%.

In specific embodiments, the orally disintegrating film matrix has a content uniformity, such that among two or more samples, the amount of second active ingredient ranges from 85% to 115%, with the standard deviation of less than or equal to 6%.

In specific embodiments, the orally disintegrating film matrix has a content uniformity, such that among two or more samples, the amount of second active ingredient ranges from 90% to 110%, with the standard deviation of less than or equal to 6%.

In specific embodiments, the first active ingredient is present in 0.1 mg/cm$^2$ to 10 mg/cm$^2$ of the orally disintegrating film matrix.

In specific embodiments, the first active ingredient is present in 0.5 mg/cm$^2$ to 7.5 mg/cm$^2$ of the orally disintegrating film matrix.

In specific embodiments, the first active ingredient is present in 0.5 mg/cm$^2$ to 5 mg/cm$^2$ of the orally disintegrating film matrix.

In specific embodiments, the first active ingredient is present in 0.75 mg/cm$^2$ to 5 mg/cm$^2$ of the orally disintegrating film matrix.

In specific embodiments, the first active ingredient is present in 1 mg/cm$^2$ to 5 mg/cm$^2$ of the orally disintegrating film matrix.

In specific embodiments, the first active ingredient is present in 5±3.5 mg/cm$^2$ of the orally disintegrating film matrix.

In specific embodiments, the first active ingredient is present in 5±3 mg/cm$^2$ of the orally disintegrating film matrix.

In specific embodiments, the first active ingredient is present in 4±2.5 mg/cm$^2$ of the orally disintegrating film matrix.

In specific embodiments, the second active ingredient is present in 0.001 mg/cm$^2$ to 0.75 mg/cm$^2$ of the orally disintegrating film matrix.

In specific embodiments, the second active ingredient is present in 0.001 mg/cm$^2$ to 0.5 mg/cm$^2$ of the orally disintegrating film matrix.

In specific embodiments, the second active ingredient is present in 0.01 mg/cm$^2$ to 0.75 mg/cm$^2$ of the orally disintegrating film matrix.

In specific embodiments, the second active ingredient is present in 0.005 mg/cm$^2$ to 0.75 mg/cm$^2$ of the orally disintegrating film matrix.

In specific embodiments, the second active ingredient is present in 0.005 mg/cm$^2$ to 0.5 mg/cm$^2$ of the orally disintegrating film matrix.

In specific embodiments, the second active ingredient is present in 0.01 mg/cm$^2$ to 0.75 mg/cm$^2$ of the orally disintegrating film matrix.

In specific embodiments, the second active ingredient is present in 0.01 mg/cm$^2$ to 0.5 mg/cm$^2$ of the orally disintegrating film matrix.

In specific embodiments, the second active ingredient is present in 0.01 mg/cm$^2$ to 0.25 mg/cm$^2$ of the orally disintegrating film matrix.

In specific embodiments, the second active ingredient is present in 0.01 mg/cm$^2$ to 0.1 mg/cm$^2$ of the orally disintegrating film matrix.

In specific embodiments, the second active ingredient is present in 0.005 mg/cm$^2$ to 0.1 mg/cm$^2$ of the orally disintegrating film matrix.

In specific embodiments, the second active ingredient is present in 0.005 mg/cm$^2$ to 0.075 mg/cm$^2$ of the orally disintegrating film matrix.

In specific embodiments, the orally disintegrating film matrix includes cellulose ether.

In specific embodiments, the orally disintegrating film matrix includes the cellulose ether hypromelose.

In specific embodiments, the orally disintegrating film matrix includes a block copolymer of polyvinyl alcohol (PVA) and polyethylene glycol (PEG).

In specific embodiments, the orally disintegrating film matrix includes the block copolymer of polyvinyl alcohol (PVA) and polyethylene glycol (PEG), Kollicoat® IR.

In specific embodiments, the orally disintegrating film matrix includes the block copolymer of polyvinyl alcohol (PVA) and polyethylene glycol (PEG), Kollicoat® Protect.

In specific embodiments, the orally disintegrating film matrix includes polyvinyl alcohol (PVA).

In specific embodiments, the orally disintegrating film matrix includes aminoalkyl methacrylate copolymers.

In specific embodiments, the orally disintegrating film matrix includes the aminoalkyl methacrylate copolymers, Eudragit® EPO.

In specific embodiments, the orally disintegrating film matrix includes methacrylic acid copolymers In specific embodiments, the orally disintegrating film matrix includes the methacrylic acid copolymers, Eudragit® L.

In specific embodiments, the rapidly dissolving binder includes a block copolymer of polyvinyl alcohol (PVA) and polyethylene glycol (PEG).

In specific embodiments, the rapidly dissolving binder includes the block copolymer of polyvinyl alcohol (PVA) and polyethylene glycol (PEG), Kollicoat® IR.

In specific embodiments, the rapidly dissolving binder includes the block copolymer of polyvinyl alcohol (PVA) and polyethylene glycol (PEG), Kollicoat® Protect.

In specific embodiments, the film forming polymer includes cellulose ethers.

In specific embodiments, the film forming polymer includes the cellulose ethers hypromelose.

In specific embodiments, the moisture deterring polymer includes aminoalkyl methacrylate copolymers.

In specific embodiments, the moisture deterring polymer includes the aminoalkyl methacrylate copolymers Eudragit® EPO.

In specific embodiments, the moisture deterring polymer includes methacrylic acid copolymers.

In specific embodiments, the orally disintegrating film matrix includes Kollicoat® and hydroxypropyl methyl cellulose (HPMC).

In specific embodiments, the orally disintegrating film matrix includes Kollicoat®, hydroxypropyl methyl cellulose (HPMC), and a pH modifying agent (e.g., acid, base, and/or buffer).

In specific embodiments, the orally disintegrating film matrix includes Kollicoat®, EUDRAGIT®, and hydroxypropyl methyl cellulose (HPMC).

In specific embodiments, the orally disintegrating film matrix includes Kollicoat®, EUDRAGIT®, hydroxypropyl methyl cellulose (HPMC), and a pH modifying agent (e.g., acid, base, and/or buffer).

In specific embodiments, the orally disintegrating film matrix includes Kollicoat®.

In specific embodiments, the orally disintegrating film matrix includes 75.26±15 wt. % Kollicoat®.

In specific embodiments, the orally disintegrating film matrix includes 73.13±15 wt. % Kollicoat®.

In specific embodiments, the orally disintegrating film matrix includes 75.26±10 wt. % Kollicoat®.

In specific embodiments, the orally disintegrating film matrix includes 73.13±10 wt. % Kollicoat®.

In specific embodiments, the orally disintegrating film matrix includes 75.26±7.5 wt. % Kollicoat®.

In specific embodiments, the orally disintegrating film matrix includes 73.13±7.5 wt. % Kollicoat®.

In specific embodiments, the orally disintegrating film matrix includes 50-80 wt. % Kollicoat®.

In specific embodiments, the orally disintegrating film matrix includes 55-80 wt. % Kollicoat®.

In specific embodiments, the orally disintegrating film matrix includes 60-80 wt. % Kollicoat®.

In specific embodiments, the orally disintegrating film matrix includes 65-80 wt. % Kollicoat®.

In specific embodiments, the Kollicoat® includes Kollicoat® Protect.

In specific embodiments, the Kollicoat® includes Kollicoat® IR.

In specific embodiments, the EUDRAGIT® includes EUDRAGIT® EPO.

In specific embodiments, the orally disintegrating film matrix includes hydroxypropyl methyl cellulose (HPMC).

In specific embodiments, the orally disintegrating film matrix includes 17.14±5 wt. % hydroxypropyl methyl cellulose (HPMC).

In specific embodiments, the orally disintegrating film matrix includes 15.26±5 wt. % hydroxypropyl methyl cellulose (HPMC).

In specific embodiments, the orally disintegrating film matrix includes 17.14±3 wt. % hydroxypropyl methyl cellulose (HPMC).

In specific embodiments, the orally disintegrating film matrix includes 15.26±3 wt. % hydroxypropyl methyl cellulose (HPMC).

In specific embodiments, the orally disintegrating film matrix includes 17.14±1.5 wt. % hydroxypropyl methyl cellulose (HPMC).

In specific embodiments, the orally disintegrating film matrix includes 15.26±1.5 wt. % hydroxypropyl methyl cellulose (HPMC).

In specific embodiments, the orally disintegrating film matrix includes 8-25 wt. % hydroxypropyl methyl cellulose (HPMC).

In specific embodiments, the orally disintegrating film matrix includes 8-20 wt. % hydroxypropyl methyl cellulose (HPMC).

In specific embodiments, the orally disintegrating film matrix includes 8-18 wt. % hydroxypropyl methyl cellulose (HPMC).

In specific embodiments, the orally disintegrating film matrix includes 8-15 wt. % hydroxypropyl methyl cellulose (HPMC).

In specific embodiments, the orally disintegrating film matrix includes 10-25 wt. % hydroxypropyl methyl cellulose (HPMC).

In specific embodiments, the orally disintegrating film matrix includes 10-20 wt. % hydroxypropyl methyl cellulose (HPMC).

In specific embodiments, the orally disintegrating film matrix includes 10-18 wt. % hydroxypropyl methyl cellulose (HPMC).

In specific embodiments, the orally disintegrating film matrix includes 10-15 wt. % hydroxypropyl methyl cellulose (HPMC).

In specific embodiments, the orally disintegrating film matrix includes EUDRAGIT®.

In specific embodiments, the orally disintegrating film matrix includes 3.87±1.5 wt. % EUDRAGIT®.

In specific embodiments, the orally disintegrating film matrix includes 3.87±1 wt. % EUDRAGIT®.

In specific embodiments, the orally disintegrating film matrix includes 3.87±0.7 wt. % EUDRAGIT®.

In specific embodiments, the orally disintegrating film matrix includes 3.87±0.5 wt. % EUDRAGIT®.

In specific embodiments, the orally disintegrating film matrix includes 3.87±0.25 wt. % EUDRAGIT®.

In specific embodiments, the orally disintegrating film matrix includes 0.5-7.5 wt. % EUDRAGIT®.

In specific embodiments, the orally disintegrating film matrix includes 0.75-7.5 wt. % EUDRAGIT®.

In specific embodiments, the orally disintegrating film matrix includes 1-7 wt. % EUDRAGIT®.

In specific embodiments, the orally disintegrating film matrix includes 1-6.5 wt. % EUDRAGIT®.

In specific embodiments, the orally disintegrating film matrix includes 1-6 wt. % EUDRAGIT®.

In specific embodiments, the orally disintegrating film matrix includes 1-5.5 wt. % EUDRAGIT®.

In specific embodiments, the orally disintegrating film matrix includes 1-5 wt. % EUDRAGIT®.

In specific embodiments, the orally disintegrating film matrix includes 1-4.5 wt. % EUDRAGIT®.

In specific embodiments, the orally disintegrating film matrix includes 1-4 wt. % EUDRAGIT®.

In specific embodiments, the orally disintegrating film matrix includes 2-7 wt. % EUDRAGIT®.

In specific embodiments, the orally disintegrating film matrix includes 2-6.5 wt. % EUDRAGIT®.

In specific embodiments, the orally disintegrating film matrix includes 2-6 wt. % EUDRAGIT®.

In specific embodiments, the orally disintegrating film matrix includes 2-5.5 wt. % EUDRAGIT®.

In specific embodiments, the orally disintegrating film matrix includes 2-5 wt. % EUDRAGIT®.

In specific embodiments, the orally disintegrating film matrix includes 2-4.5 wt. % EUDRAGIT®.

In specific embodiments, the orally disintegrating film matrix includes 2-4 wt. % EUDRAGIT®.

In specific embodiments, the Kollicoat® is at least one of Kollicoat® Protect (polyvinyl alcohol-polyethylene glycol graft-copolymer and polyvinyl alcohol (PVA)), Kollicoat® IR (macrogol-poly(vinyl alcohol) graft-copolymer, polyvinyl alcohol-polyethylene glycol graft-copolymer), Kollicoat® MAE 100 P (methacrylic acid-ethyl acrylate copolymer (1:1)), Kollicoat® MAE 30 DP (methacrylic acid copolymer dispersion, methacrylic acid-ethyl acrylate copolymer (1:1) dispersion 30%), and Kollicoat® SR 30 D (poly(vinyl acetate) dispersion 30 wt. %, poly(vinyl acetate) stabilized with polyvinylpyrrolidone and sodium lauryl sulfate).

In specific embodiments, the Kollicoat® is Kollicoat® Protect (polyvinyl alcohol-polyethylene glycol graft-copolymer and polyvinyl alcohol (PVA)).

In specific embodiments, the EUDRAGIT® is at least one of EUDRAGIT® E 100, EUDRAGIT® E 12,5, EUDRAGIT® EPO, and EUDRAGIT® EPO ReadMix.

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 15 wt. % |
| Hypromellose 2910 USP | 20 ± 6.5 wt. % |
| Citric Acid Anhydrous, USP | 4 ± 1.5 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 10 wt. % |
| Hypromellose 2910 USP | 20 ± 5 wt. % |
| Citric Acid Anhydrous, USP | 4 ± 1.25 wt. % |

In specific embodiments, the orally disintegrating film matrix includes:

| Ingredient | Amount in strip |
| --- | --- |
| Water, Purified USP | 4 ± 2 wt. % |
| Kollicoat ® Protect | 75 ± 7.5 wt. % |
| Hypromellose 2910 USP | 17 ± 3.5 wt. % |
| Citric Acid Anhydrous, USP | 4 ± 1 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 15 wt. % |
| Hypromellose 2910 USP | 20 ± 6.5 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 10 wt. % |
| Hypromellose 2910 LISP | 20 ± 5 wt. % |

In specific embodiments, the orally disintegrating film matrix includes:

| Ingredient | Amount in strip |
| --- | --- |
| Water, Purified USP | 4 ± 2 wt. % |
| Kollicoat ® Protect | 75 ± 7.5 wt. % |
| Hypromellose 2910 USP | 17 ± 3.5 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 15 wt. % |
| Hypromellose 2910 USP | 15 ± 5 wt. % |
| EUDRAGIT ® EPO | 5 ± 3 wt. % |
| Citric Acid Anhydrous, USP | 4 ± 1.5 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 10 wt. % |
| Hypromellose 2910 USP | 15 ± 10 wt. % |
| EUDRAGIT ® EPO | 5 ± 2 wt. % |
| Citric Acid Anhydrous, USP | 4 ± 1.25 wt. % |

In specific embodiments, the orally disintegrating film matrix includes:

| Ingredient | Amount in strip |
| --- | --- |
| Water, Purified USP | 4 ± 7 wt. % |
| Kollicoat ® Protect | 73 ± 7.5 wt. % |
| Hvpromellose 2910 USP | 15 ± 10 wt. % |
| EUDRAGIT ® EPO | 4 ± 1.5 wt. % |
| Citric Acid Anhydrous, USP | 4 ± 1 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 15 wt. % |
| Hypromellose 2910 USP | 15 ± 5 wt. % |
| EUDRAGIT ® EPO | 5 ± 3 wt. % |

In specific embodiments, the orally disintegrating film matrix includes:

| Ingredient | Amount in strip |
| --- | --- |
| Water, Purified USP | 5 ± 3 wt. % |
| Kollicoat ® Protect | 75 ± 10 wt. % |
| Hypromellose 2910 UST | 15 ± 10 wt. % |
| EUDRAGIT ® EPO | 5 ± 2 wt. % |

In specific embodiments, the orally disintegrating film matrix includes:

| Ingredient | Amount in strip |
| --- | --- |
| Water, Purified USP | 4 ± 2 wt. % |
| Kollicoat ® Protect | 73 ± 7.5 wt. % |
| Hypromellose 2910 USP | 15 ± 10 wt. % |
| EUDRAGIT ® EPO | 4 ± 1.5 wt. % |

In specific embodiments, the orally disintegrating film matrix includes at least one of plasticizer, preservative, solvent, coloring agent, flavoring agent, sweetening agent, filler, bulking agent, saliva stimulating agent, stabilizing and thickening agent, gelling agent, taste masking agent, pigment, lubricant, release modifier, adjuvant, solubilizer & emulsifier, fragrance, emulsifier, surfactant, pH adjusting agent, buffering agent, lipid, glidant, stabilizer, antioxidant, anti-tacking agent, and humectant.

In specific embodiments, the storing can be up to a few days (e.g., 1-5 days).

In specific embodiments, the storing can be up to 90 days.

In specific embodiments, the storing can be an extended period of time (e.g., up to several months).

In specific embodiments, the storing can be 1-12 months.

In specific embodiments, the storing can be 1-6 months.

In specific embodiments, the storing can be 1-3 months.

In specific embodiments, the pH adjusting agent can include an acid (e.g., inorganic acid or organic acid) or base (e.g., inorganic base or organic base).

In specific embodiments, the pH adjusting agent can include citric acid.

In specific embodiments, the orally disintegrating film matrix includes a second active ingredient impregnated to the orally disintegrating film matrix.

In specific embodiments, the orally disintegrating film matrix includes a second active ingredient impregnated to the orally disintegrating film matrix via 3D printing.

In specific embodiments, the orally disintegrating film matrix includes a second active ingredient impregnated to the orally disintegrating film matrix via 3D printing selected from the group consisting of Vat Polymerization (VP), Powder Bed Fusion (PBF), Material Extrusion (ME), Material Jetting (MJ), and Direct Energy Deposition (DED).

In specific embodiments, the orally disintegrating film matrix includes a second active ingredient impregnated to the orally disintegrating film matrix via 3D printing selected from the group consisting of Stereolithography (SLA), Digital Light Processing (DLP), 2-Photon Polymerization (2PP), Continuous Liquid Interface Production (CLIP), Selective Laser Sintering (SLS), Selective Laser Melting (SLM), Electron Beam Melting (EBM), Multi Jet Fusion (MJF), Fused Deposition Modelling (FDM), Pneumatic Extrusion/Syringe Extrusion (PE/SE), Material Jetting (MJ), Nano Particle Jetting (NPJ), Drop on Demand (DoD), Binder Jetting (BJ), Laser Engineered Net Shape (LENS), and Electron Beam Additive Manufacture (EMAM).

In specific embodiments, the orally disintegrating film matrix includes a second active ingredient impregnated to the orally disintegrating film matrix via spraying, lithographic printing, ink jet printing, electrostatic dry powder coating, atomic layer deposition, corona charging, tribo charging, magnetically assisted impacting coating (MAIC), vacuum film coating, gas jet drying, or electrohydrodynamic atomization (EHDA) processes.

In specific embodiments, the orally disintegrating film matrix includes printed indicia visible on the orally disintegrating film matrix.

In specific embodiments, the orally disintegrating film matrix includes printed indicia impregnated to the orally disintegrating film matrix.

In specific embodiments, the orally disintegrating film matrix includes printed indicia impregnated to the orally disintegrating film matrix via 3D printing.

In specific embodiments, the orally disintegrating film matrix includes printed indicia impregnated to the orally disintegrating film matrix via 3D printing selected from the group consisting of Vat Polymerization (VP), Powder Bed Fusion (PBF), Material Extrusion (ME), Material Jetting (MJ), and Direct Energy Deposition (DED).

In specific embodiments, the orally disintegrating film matrix includes printed indicia impregnated to the orally disintegrating film matrix via 3D printing selected from the group consisting of Stereolithography (SLA), Digital Light Processing (DLP), 2-Photon Polymerization (2PP), Continuous Liquid Interface Production (CLIP), Selective Laser Sintering (SLS), Selective Laser Melting (SLM), Electron Beam Melting (EBM), Multi Jet Fusion (MJF), Fused Deposition Modelling (FDM), Pneumatic Extrusion/Syringe Extrusion (PE/SE), Material Jetting (MJ), Nano Particle Jetting (NPJ), Drop on Demand (DoD), Binder Jetting (BJ), Laser Engineered Net Shape (LENS), and Electron Beam Additive Manufacture (EMAM).

In specific embodiments, the orally disintegrating film matrix includes printed indicia impregnated to the orally disintegrating film matrix via spraying, lithographic printing, ink jet printing, electrostatic dry powder coating, atomic layer deposition, corona charging, tribo charging, magnetically assisted impacting coating (MAIC), vacuum film coating, gas jet drying, or electrohydrodynamic atomization (EHDA) processes.

In specific embodiments, the orally disintegrating film matrix is formed from a slurry that includes a first active ingredient (e.g., the homogeneous mixture in (a) includes a first active ingredient).

In specific embodiments, the orally disintegrating film matrix is formed from a slurry that does not include a first active ingredient (e.g., the homogeneous mixture in (a) does not include a first active ingredient).

In specific embodiments, the orally disintegrating film matrix is formed from a slurry that includes

| Ingredient | Amount in slurry |
| --- | --- |
| Water, Purified USP | 82.00 ± 12 wt. % |
| Kollicoat ® Protect | 14.05 ± 5 wt. % |
| Hypromellose 2910 USP | 3.20 ± 1.5 wt. % |
| Citric Acid Anhydrous, USP | 0.75 ± 0.40 wt. % |

In specific embodiments, the orally disintegrating film matrix is formed from a slurry that includes

| Ingredient | Amount in slurry |
| --- | --- |
| Water, Purified USP | 82.00 ± 8 wt,% |
| Kollicoat ® Protect | 14.05 ± 3 wt. % |
| Hypromellose 2910 USP | 3.20 ± 1 wt. % |
| Citric Acid Anhydrous, USP | 0.75 ± 0.35 wt. % |

In specific embodiments, the orally disintegrating film matrix is formed from a slurry that includes

| Ingredient | Amount in slurry |
| --- | --- |
| Water, Purified USP | 82.00 ± 5 wt. % |
| Kollicoat ® Protect | 14.05 ± 2 wt. % |
| Hypromellose 2910 USP | 3.20 ± 0.5 wt. % |
| Citric Acid Anhydrous, USP | 0.75 ± 0.25 wt. % |

In specific embodiments, the orally disintegrating film matrix is formed from a slurry that includes

| Ingredient | Amount in slurry |
|---|---|
| Water, Purified USP | 70-85 wt. % |
| Kollicoat ® Protect | 5-15 wt. % |
| Hypromellose 2910 USP | 0.5-4.5 wt. % |
| Citric Acid Anhydrous, USP | 0.75 ± 0.1 wt. % |

In specific embodiments, the orally disintegrating film matrix is formed from a slurry that includes

| Ingredient | Amount in slurry |
|---|---|
| Water, Purified USP | 82.00 ± 12 wt. % |
| Kollicoat ® Protect | 14.05 ± 5 wt. % |
| Hypromellose 2910 USP | 3.20 ± 1.5 wt. % |

In specific embodiments, the orally disintegrating film matrix is formed from a slurry that includes

| Ingredient | Amount in slurry |
|---|---|
| Water, Purified USP | 82.00 ± 8 wt. % |
| Kollicoat ® Protect | 14.05 ± 3 wt. % |
| Hypromellose 2910 USP | 3.20 ± 1 wt. % |

In specific embodiments, the orally disintegrating film matrix is formed from a slurry that includes

| Ingredient | Amount in slurry |
|---|---|
| Water, Purified USP | 82.00 ± 5 wt. % |
| Kollicoat ® Protect | 14.05 ± 2 wt. % |
| Elypromefiose 2910 UST | 3.20 ± 0.5 wt. % |

In specific embodiments, the orally disintegrating film matrix is formed from a slurry that includes

| Ingredient | Amount in slurry |
|---|---|
| Water, Purified USP | 70-85 wt. % |
| Kollicoat ® Protect | 5-15 wt. % |
| Hypromellose 2910 USP | 0.5-4.5 wt. % |

In specific embodiments, the orally disintegrating film matrix is formed from a slurry that includes

| Ingredient | Amount in slurry |
|---|---|
| Water, Purified USP | 81.00 ± 12 wt. % |
| Kollicoat ® Protect | 14.38 ± 5 wt. % |
| Hypromellose 2910 USP | 3.20 ± 1.5 wt. % |
| EUDRAGIT ® EPO | 4 ± 1.5 wt. % |
| Citric Acid Anhydrous, USP | 0.75 ± 0.35 wt. % |

In specific embodiments, the orally disintegrating film matrix is formed from a slurry that includes

| Ingredient | Amount in slurry |
|---|---|
| Water, Purified LISP | 81.00 ± 8 wt. % |
| Kollicoat ® Protect | 14.38 ± 3 wt. % |
| Hypromellose 2910 USP | 3.20 ± 1 wt. % |
| EUDRAGIT ® EPO | 4 ± 1 wt. % |
| Citric Acid Anhydrous, USP | 0.75 ± 0.25 wt. % |

In specific embodiments, the orally disintegrating film matrix is formed from a slurry that includes

| Ingredient | Amount in slurry |
|---|---|
| Water, Purified USP | 81.00 ± 5 wt. % |
| Kollicoat ® Protect | 14.38 ± 2 wt. % |
| Hypromellose 2910 USP | 3.20 ± 0.5 wt. % |
| EUDRAGIT ® EPO | 4 ± 0.5 wt. % |
| Citric Acid Anhydrous, USP | 0.75 ± 0.1 wt. % |

In specific embodiments, the orally disintegrating film matrix is formed from a slurry that includes

| Ingredient | Amount in slurry |
|---|---|
| Water, Purified USP | 70-85 wt. % |
| Kollicoat ® Protect | 5-15 wt. % |
| Hypromellose 2910 USP | 0.5-4.5 wt. % |
| EUDRAGIT ® EPO | 0.5-4.5 wt. % |
| Citric Acid Anhydrous, USP | 0.75 ± 0.1 wt. % |

In specific embodiments, the orally disintegrating film matrix is formed from a slurry that includes

| Ingredient | Amount in slurry |
|---|---|
| Water, Purified USP | 81.00 ± 12 wt. % |
| Kollicoat ® Protect | 14.38 ± 5 wt. % |
| Hypromellose 2910 USP | 3.20 ± 1.5 wt. % |
| EUDRAGIT ® EPO | 4 ± 1.5 wt. % |

In specific embodiments, the orally disintegrating film matrix is formed from a slurry that includes

| Ingredient | Amount in slurry |
|---|---|
| Water, Purified USP | 81.00 ± 8 wt. % |
| Kollicoat ® Protect | 14.38 ± 3 wt. % |
| Hypromellose 2910 USP | 3.20 ± 1 wt. % |
| EUDRAGIT ® EPO | 4 ± 1 wt. % |

In specific embodiments, the orally disintegrating film matrix is formed from a slurry that includes

| Ingredient | Amount in slurry |
|---|---|
| Water, Purified USP | 81.00 ± 5 wt. % |
| Kollicoat ® Protect | 14.38 ± 2 wt. % |
| Hypromellose 2910 USP | 3.20 ± 0.5 wt. % |
| EUDRAGIT ® EPO | 4 ± 0.5 wt. % |

In specific embodiments, the orally disintegrating film matrix is formed from a slurry that includes

| Ingredient | Amount in slurry |
|---|---|
| Water, Purified USP | 70-85 wt. % |
| Kollicoat ® Protect | 5-15 wt. % |
| Hypromellose 2910 USP | 0.5-4.5 wt. % |
| EUDRAGIT ® EPO | 0.5-4.5 wt. % |

In specific embodiments, the orally disintegrating film matrix is orally administered to a subject.

In specific embodiments, the orally disintegrating film matrix is orally administered to a subject, such that the one or more active ingredients are delivered orally.

In specific embodiments, the orally disintegrating film matrix is orally administered to a subject, such that the one or more active ingredients are delivered enterally.

In specific embodiments, the orally disintegrating film matrix is orally administered to a subject, such that the one or more active ingredients are delivered sublingually.

In specific embodiments, the orally disintegrating film matrix is orally administered to a subject, such that the one or more active ingredients are delivered buccally.

In specific embodiments, the orally disintegrating film matrix is orally administered to a subject, such that the one or more active ingredients are delivered transmucosally.

In specific embodiments, the subject is a human.

In specific embodiments, the subject is a human child of less than 12 years old.

In specific embodiments, the subject is a human adult of at least 18 years old.

In specific embodiments, the subject is a human adolescent of 12 to 18 years old.

Enumerated Embodiments

Specific enumerated embodiments [1] to [86] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] An orally disintegrating film matrix that includes:
  rapidly dissolving binder; and
  film forming polymer;
wherein,
  the orally disintegrating film matrix has a moisture content of less than 8 wt. %; and
  upon contact with the oral cavity, the orally disintegrating film matrix film disintegrates within 60 seconds.

[2.] The orally disintegrating film matrix of embodiment [1], which does not include a first active ingredient.

[3.] The orally disintegrating film matrix of embodiment [1], that further includes a first active ingredient.

[4.] An orally disintegrating film matrix that includes:
  first active ingredient;
  rapidly dissolving binder; and
  film forming polymer;
wherein,
  the orally disintegrating film matrix has a moisture content of less than 8 wt. %, and
  upon contact with the oral cavity, the orally disintegrating film matrix disintegrates within 60 seconds.

[5.] A method of forming an orally disintegrating film matrix that includes:
  (a) contacting water, a rapidly dissolving binder, and a film forming polymer, to form a homogeneous mixture;
  (b) extruding the homogeneous mixture onto a substrate;
  (c) curing the extruded homogeneous mixture to form the orally disintegrating film matrix; and
  (d) optionally sizing the orally disintegrating film matrix to a desired surface area.

[6.] The method of embodiment [5], wherein the homogeneous mixture in (a) does not include a first active ingredient.

[7.] The method of embodiment [5], wherein the homogeneous mixture in (a) that further includes a first active ingredient.

[8.] A method of forming an orally disintegrating film matrix that includes:
  (a) contacting water, a first active ingredient, a rapidly dissolving binder, and a film forming polymer, to form a homogeneous mixture;
  (b) extruding the homogeneous mixture onto a substrate,
  (c) curing the extruded homogeneous mixture to form the orally disintegrating film matrix; and
  (d) optionally sizing the orally disintegrating film matrix to a desired surface area.

[9.] A kit that includes
  (a) the orally disintegrating film matrix of any one of embodiments [1]-[4] or the orally disintegrating film matrix obtained by the method of any one of embodiments [5]-[8];
  (b) a sealable and vapor impermeable container closure system;
wherein,
  the orally disintegrating film matrix is contained within the sealable and vapor impermeable container closure system.

[10.] A method of delivering an active ingredient to a subject in need thereof, the method includes orally administering to the subject the orally disintegrating film matrix of any one of embodiments [1]-[4], or the orally disintegrating film matrix obtained by the method of any one of embodiments [5]-[8].

[11.] The orally disintegrating film matrix of any one of the preceding embodiments, further includes a moisture deterring polymer.

[12.] The orally disintegrating film matrix of embodiment [11], wherein the moisture deterring polymer includes aminoalkyl methacrylate copolymers.

[13.] The orally disintegrating film matrix of embodiment [11], wherein the moisture deterring polymer includes methacrylic acid copolymers.

[14.] The orally disintegrating film matrix of embodiment [11], wherein the moisture deterring polymer includes EUDRAGIT® EPO.

[15.] The orally disintegrating film matrix of embodiment [11], wherein the moisture deterring polymer includes 0.5-5 wt. % EUDRAGIT® EPO.

[16.] The orally disintegrating film matrix of embodiment [11], wherein the moisture deterring polymer includes 1-4 wt. % EUDRAGIT® EPO.

[17.] The orally disintegrating film matrix of any one of the preceding embodiments, wherein the rapidly dissolving binder includes a block copolymer of polyvinyl alcohol (PVA) and polyethylene glycol (PEG).

[18.] The orally disintegrating film matrix of any one of the preceding embodiments, wherein the rapidly dissolving binder includes a polyvinyl alcohol (PVA)-polyethylene glycol (PEG) graft copolymer.

[19.] The orally disintegrating film matrix of any one of the preceding embodiments, wherein the rapidly dissolving binder includes combination of (a) polyvinyl alcohol (PVA) and (b) a polyvinyl alcohol (PVA)-polyethylene glycol (PEG) graft copolymer.

[20.] The orally disintegrating film matrix of any one of the preceding embodiments, wherein the rapidly dissolving binder includes Kollicoat® Protect.

[21.] The orally disintegrating film matrix of any one of the preceding embodiments, wherein the rapidly dissolving binder includes 40-80 wt. % Kollicoat® Protect.

[22.] The orally disintegrating film matrix of any one of the preceding embodiments, wherein the film forming polymer includes cellulose ethers.

[23.] The orally disintegrating film matrix of any one of the preceding embodiments, wherein the film forming polymer includes Hypromellose.

[24.] The orally disintegrating film matrix of any one of the preceding embodiments, wherein the film forming polymer includes 5-20 wt. % Hypromellose.

[25.] The orally disintegrating film matrix of any one of the preceding embodiments, that further includes at least one of plasticizer, preservative, solvent, coloring agent, flavoring agent, sweetening agent, filler, bulking agent, saliva stimulating agent, stabilizing and thickening agent, gelling agent, taste masking agent, pigment, lubricant, release modifier, adjuvant, solubilizer & emulsifier, fragrance, emulsifier, surfactant, lipid, glidant, stabilizer, antioxidant, anti-tacking agent, acid, base, buffer, and humectant.

[26.] The orally disintegrating film matrix of any one of the preceding embodiments, that further includes a second active ingredient impregnated to the orally disintegrating film matrix.

[27.] The orally disintegrating film matrix of any one of the preceding embodiments, that further includes a second active ingredient impregnated to the orally disintegrating film matrix via 3D printing.

[28.] The orally disintegrating film matrix of any one of the preceding embodiments, that further includes a second active ingredient impregnated to the orally disintegrating film matrix via 3D printing selected from the group consisting of Vat Polymerization (VP), Powder Bed Fusion (PBF), Material Extrusion (ME), Material Jetting (MJ), and Direct Energy Deposition (DED).

[29.] The orally disintegrating film matrix of any one of the preceding embodiments, that further includes a second active ingredient impregnated to the orally disintegrating film matrix via 3D printing selected from the group consisting of Stereolithography (SLA), Digital Light Processing (DLP), 2-Photon Polymerization (2PP), Continuous Liquid Interface Production (CLIP), Selective Laser Sintering (SLS), Selective Laser Melting (SLM), Electron Beam Melting (EBM), Multi Jet Fusion (MJF), Fused Deposition Modelling (FDM), Pneumatic Extrusion/Syringe Extrusion (PE/SE), Material Jetting (MJ), Nano Particle Jetting (NPJ), Drop on Demand (DoD), Binder Jetting (BJ), Laser Engineered Net Shape (LENS), and Electron Beam Additive Manufacture (EMAM).

[30.] The orally disintegrating film matrix of any one of the preceding embodiments, that further includes a second active ingredient impregnated to the orally disintegrating film matrix via spraying, lithographic printing, ink jet printing, electrostatic dry powder coating, atomic layer deposition, corona charging, tribo charging, magnetically assisted impacting coating (MAIC), vacuum film coating, gas jet drying, or electrohydrodynamic atomization (EHDA) processes.

[31.] The orally disintegrating film matrix of any one of the preceding embodiments, wherein the first active ingredient is moisture sensitive.

[32.] The orally disintegrating film matrix of any one of the preceding embodiments, wherein the first active ingredient is oxygen sensitive.

[33.] The orally disintegrating film matrix of any one of the preceding embodiments, wherein the first active ingredient is pH sensitive.

[34.] The orally disintegrating film matrix of any one of the preceding embodiments, wherein the first active ingredient is heat sensitive.

[35.] The orally disintegrating film matrix of any one of the preceding embodiments, wherein the first active ingredient is light (UV) sensitive.

[36.] The orally disintegrating film matrix of any one of the preceding embodiments, wherein the first active ingredient has an unpleasant taste or odor.

[37.] The orally disintegrating film matrix of any one of the preceding embodiments, wherein the first active ingredient is water-insoluble.

[38.] The orally disintegrating film matrix of any one of the preceding embodiments, wherein the first active ingredient is present in a small quantity.

[39.] The orally disintegrating film matrix of any one of the preceding embodiments, wherein the second active ingredient is moisture sensitive.

[40.] The orally disintegrating film matrix of any one of the preceding embodiments, wherein the second active ingredient is oxygen sensitive.

[41.] The orally disintegrating film matrix of any one of the preceding embodiments, wherein the second active ingredient is pH sensitive.

[42.] The orally disintegrating film matrix of any one of the preceding embodiments, wherein the second active ingredient is heat sensitive.

[43.] The orally disintegrating film matrix of any one of the preceding embodiments, wherein the second active ingredient is light (UV) sensitive.

[44.] The orally disintegrating film matrix of any one of the preceding embodiments, wherein the second active ingredient has an unpleasant taste or odor.

[45.] The orally disintegrating film matrix of any one of the preceding embodiments, wherein the second active ingredient is water-insoluble.

[46.] The orally disintegrating film matrix of any one of the preceding embodiments, wherein the second active ingredient is present in a small quantity.

[47.] The orally disintegrating film matrix of any one of the preceding embodiments, wherein the first and second active ingredients are the same.

[48.] The orally disintegrating film matrix of any one of the preceding embodiments, wherein the first and second active ingredients are different.

[49.] The orally disintegrating film matrix of any one of the preceding embodiments, wherein the first active ingredient includes a cannabinoid, terpene, or combination thereof.

[50.] The orally disintegrating film matrix of any one of the preceding embodiments, wherein the first active ingredient includes CBD (cannabidiol).

[51.] The orally disintegrating film matrix of any one of the preceding embodiments, wherein the first active ingredient includes 15 mg CBD.

[52.] The orally disintegrating film matrix of any one of the preceding embodiments, wherein the first active ingredient includes Beta-Caryophyllene.

[53.] The orally disintegrating film matrix of any one of the preceding embodiments, wherein the first active ingredient is present in 5-70 mg.

[54.] The orally disintegrating film matrix of any one of the preceding embodiments, wherein the first active ingredient is present in 5-50 mg.

[55.] The orally disintegrating film matrix of any one of the preceding embodiments, wherein the first active ingredient is present in 15±10 mg.

[56.] The orally disintegrating film matrix of any one of the preceding embodiments, wherein the first active ingredient is present in 15±5 mg.

[57.] The orally disintegrating film matrix of any one of the preceding embodiments, wherein the first active ingredient is present in 1-30 wt. %.

[58.] The orally disintegrating film matrix of any one of the preceding embodiments, wherein the first active ingredient is present in 2-20 wt. %.

[59.] The orally disintegrating film matrix of any one of the preceding embodiments, wherein the first active ingredient is present in 10±5 wt. %.

[60.] The orally disintegrating film matrix of any one of the preceding embodiments, wherein the second active ingredient is present in 0.01-1 mg.

[61.] The orally disintegrating film matrix of any one of the preceding embodiments, wherein the second active ingredient is present in 0.01-0.5 mg.

[62.] The orally disintegrating film matrix of any one of the preceding embodiments, wherein the second active ingredient is present in 0.3±0.25 mg.

[63.] The orally disintegrating film matrix of any one of the preceding embodiments, wherein the second active ingredient is present in 0.3±0.1 mg.

[64.] The orally disintegrating film matrix of any one of the preceding embodiments, wherein the second active ingredient is present in 0.1-3 wt. %.

[65.] The orally disintegrating film matrix of any one of the preceding embodiments, wherein the second active ingredient is present in 0.2-2 wt. %.

[66.] The orally disintegrating film matrix of any one of the preceding embodiments, wherein the second active ingredient is present in 1±0.5 wt. %.

[67.] The orally disintegrating film matrix of any one of the preceding embodiments, having a mass of 200±50 mg.

[68.] The orally disintegrating film matrix of any one of the preceding embodiments, having the following dimensions: 44±6 mm×22±3 mm×0.12±0.02 mm (4.4±0.6 cm×2.2±0.3 cm×0.012±0.002 cm).

[69.] The orally disintegrating film matrix of any one of the preceding embodiments, having a thickness of less than 0.150 mm.

[70.] The orally disintegrating film matrix of any one of the preceding embodiments, having a content uniformity, such that among two or more samples, the amount of first active ingredient ranges from 85% to 115%, with the standard deviation of less than or equal to 6%.

[71.] The orally disintegrating film matrix of any one of the preceding embodiments, having a content uniformity, such that among two or more samples, the amount of second active ingredient ranges from 85% to 115%, with the standard deviation of less than or equal to 6%.

[72.] The orally disintegrating film matrix of any one of the preceding embodiments, containing the first active ingredient in 0.5 mg/cm$^2$ to 5 mg/cm$^2$.

[73.] The orally disintegrating film matrix of any one of the preceding embodiments, containing the second active ingredient in 0.001 mg/cm$^2$ to 0.5 mg/cm$^2$.

[74.] The method of forming the orally disintegrating film matrix of any one of the preceding embodiments, wherein the homogeneous mixture in (a) further includes a first active ingredient.

[75.] The method of forming the orally disintegrating film matrix of any one of the preceding embodiments, wherein the homogeneous mixture in (a) does not include an active ingredient.

[76.] The method of forming the orally disintegrating film matrix of any one of the preceding embodiments, that further includes, after the curing of the extruded homogeneous mixture to form the orally disintegrating film matrix, impregnating to the orally disintegrating film matrix a second active ingredient.

[77.] The method of forming the orally disintegrating film matrix of any one of the preceding embodiments, that further includes, after the curing of the extruded homogeneous mixture to form the orally disintegrating film matrix, impregnating to the orally disintegrating film matrix via 3D printing a second active ingredient.

[78.] The method of forming the orally disintegrating film matrix of any one of the preceding embodiments, that further includes, after the curing of the extruded homogeneous mixture to form the orally disintegrating film matrix, impregnating to the orally disintegrating film matrix via 3D printing a second active ingredient, wherein the 3D printing is selected from the group consisting of Vat Polymerization (VP), Powder Bed Fusion (PBF), Material Extrusion (ME), Material Jetting (MJ), and Direct Energy Deposition (DED).

[79.] The method of forming the orally disintegrating film matrix of any one of the preceding embodiments, that further includes, after the curing of the extruded homogeneous mixture to form the orally disintegrating film matrix, impregnating to the orally disintegrating film matrix via 3D printing a second active ingredient, wherein the 3D printing is selected from the group consisting of Stereolithography (SLA), Digital Light Processing (DLP), 2-Photon Polymerization (2PP), Continuous Liquid Interface Production (CLIP), Selective Laser Sintering (SLS), Selective Laser Melting (SLM), Electron Beam Melting (EBM), Multi Jet Fusion (MJF), Fused Deposition Modelling (FDM), Pneumatic Extrusion/Syringe Extrusion (PE/SE), Material Jetting (MJ), Nano Particle Jetting (NPJ), Drop on Demand (DoD), Binder Jetting (BJ), Laser Engineered Net Shape (LENS), and Electron Beam Additive Manufacture (EMAM).

[80.] The method of forming the orally disintegrating film matrix of any one of the preceding embodiments, that further includes, after the curing of the extruded homogeneous mixture to form the orally disintegrating film matrix, impregnating to the orally disintegrating film matrix a second active ingredient, via spraying, lithographic printing, ink jet printing, electrostatic dry powder coating, atomic layer deposition, corona charging, tribo charging, magnetically assisted impacting coating (MAIC), vacuum film coating, gas jet drying, or electrohydrodynamic atomization (EHDA) processes.

[81.] The method of forming the orally disintegrating film matrix of any one of the preceding embodiments, that further includes, after the curing of the extruded homogeneous mixture to form the orally disintegrating film matrix, impregnating to the orally disintegrating film matrix printed indicia.

[82.] The method of forming the orally disintegrating film matrix of any one of the preceding embodiments, that further includes, after the curing of the extruded homogeneous mixture to form the orally disintegrating film matrix, impregnating printed indicia to the orally disintegrating film matrix via 3D printing.

[83.] The method of forming the orally disintegrating film matrix of any one of the preceding embodiments, that further includes, after the curing of the extruded homogeneous mixture to form the orally disintegrating film matrix, impregnating printed indicia to the orally disintegrating film matrix via 3D printing, wherein the 3D printing is selected from the group consisting of Vat Polymerization (VP), Powder Bed Fusion (PBF), Material Extrusion (ME), Material Jetting (MJ), and Direct Energy Deposition (DED).

[84.] The method of forming the orally disintegrating film matrix of any one of the preceding embodiments, that further includes, after the curing of the extruded homogeneous mixture to form the orally disintegrating film matrix, impregnating printed indicia to the orally disintegrating film matrix via 3D printing, wherein the 3D printing is selected from the group consisting of Stereolithography (SLA), Digital Light Processing (DLP), 2-Photon Polymerization (2PP), Continuous Liquid Interface Production (CLIP), Selective Laser Sintering (SLS), Selective Laser Melting (SLM), Electron Beam Melting (EBM), Multi Jet Fusion (MJF), Fused Deposition Modelling (FDM), Pneumatic Extrusion/Syringe Extrusion (PE/SE), Material Jetting (MJ), Nano Particle Jetting (NPJ), Drop on Demand (DoD), Binder Jetting (BJ), Laser Engineered Net Shape (LENS), and Electron Beam Additive Manufacture (EMAM).

[85.] The method of forming the orally disintegrating film matrix of any one of the preceding embodiments, that further includes, after the curing of the extruded homogeneous mixture to form the orally disintegrating film matrix, impregnating printed indicia to the orally disintegrating film matrix, via spraying, lithographic printing, ink jet printing, electrostatic dry powder coating, atomic layer deposition, corona charging, tribo charging, magnetically assisted impacting coating (MAIC), vacuum film coating, gas jet drying, or electrohydrodynamic atomization (EHDA) processes.

[86.] The method of forming the orally disintegrating film matrix of any one of embodiments [81]-[85], wherein the printed indicia includes at least one of a letter, word, marking, design, logo, symbol, image, product name, active ingredient(s), strength, manufacturer company name, marketing company name, manufacturer company logo, marketing company logo, instructions of use, and product warnings.

EXAMPLES

Example 1: Method of Manufacturing Low Moisture Rapid Dissolving Film

1. Weigh out the amounts of water, Kollicoat® Protect, hydroxypropyl methyl cellulose, and citric acid.
2. Blend the water and citric acid together until the solution is homogenous.
3. Add the hydroxypropyl methyl cellulose to the existing solution and blend thoroughly until the solution is homogenous.
4. Add the Kollicoat® Protect to the existing solution and blend thoroughly until the solution is homogenous.
5. Extrude the solution at 400-800 mcm onto semi-permeable paper substrate and place in the oven to cure the film.
6. Range of temperature: 180° F.–260° F.
7. After the film is dried, apply the active ingredient(s).
8. Cut the sheet into the desired surface area (individual dosages). Target film size: 24 mm×31 mm.

Example 2: Method of Manufacturing Low Moisture Rapid Dissolving Film

A. Dispensing

The following raw materials were dispensed in its given amounts in separate containers:

| Material No. | Ingredient | % w/w | Amount (g) |
|---|---|---|---|
| S1028 | Water, Purified USP | 81.00% | 81.00 |
| S1198 | Kollicoat ® Protect | 14.38% | 14.38 |
| S1167 | Hypromellose 2910 USP | 3.00% | 3.00 |
| S1006 | Citric Acid Anhydrous, USP | 0.86% | 0.86 |
| N/A | EUDRAGIT ® EPO | 0.76% | 0.76 |
| | Total | 100.00% | 100.00% |

B. Blending

The blending of the materials was carried out as follows:
1. Begin blending water in a 500 ml beaker using the overhead mixer.
2. Add the following materials in sequential order. Blend each material until slurry is homogenous.
   a. Citric Acid (S1006)
   b. Eudragit® EPO
   c. Hypromellose (S1167)
   d. Kollicoat® Protect (S1011)

C. Curing

The slurry was cured in an R&D laboratory oven as follows:
1. Set R&D laboratory oven to 170° F.
2. Adjust Gardco extruder to pin gauge between 400-800 mcm.
3. Extrude the slurry onto siliconized paper using Gardco extruder.
4. Place siliconized paper into R&D laboratory oven for 10-20 minutes.

D. Cutting

The film was cut as follows:
1. Use razor blade and straight edge to cut film to desired dimensions.

Example 3: Method of Manufacturing Low Moisture Rapid Dissolving Film

A. Dispensing

The following raw materials were dispensed in its given amounts in separate containers:

| Material No. | Ingredient | % w/w | Amount (g) |
|---|---|---|---|
| S1028 | Water, Purified USP | 82.00% | 82.00 |
| S1198 | Kollicoat ® Protect | 14.05% | 14.05 |
| S1167 | Hypromellose 2910 USP | 3.20% | 3.20 |
| S1006 | Citric Acid Anhydrous, USP | 0.75% | 0.75 |
| | Total | 100.00% | 100.00% |

B. Blending

The blending of the materials was carried out as follows:
1. Begin blending water in a 500 ml beaker using the overhead mixer.

2. The following materials were added in sequential order. Blend each material until slurry is homogenous.
   a. Citric Acid (S1006)
   b. Hypromellose (S1167)
   c. Kollicoat® Protect (S1011)

C. Curing

The slurry was cured in an R&D laboratory oven as follows:
1. Set R&D laboratory oven to 170° F.
2. Adjust Gardco extruder to pin gauge between 400-800 mcm.
3. Extrude the slurry onto siliconized paper using Gardco extruder.
4. Place siliconized paper into R&D laboratory oven for 10-20 minutes.

D. Cutting

The film was cut as follows:
1. Use razor blade and straight edge to cut film to desired dimensions.

Example 4

Exemplary oral dissolving films targeting specific combination of (i) low moisture, (ii) rapidly dissolving (<10 sec), (iii) target pH of 4.6-5, and (iv) suitable taste mask without addition of taste masking agent or sweetener.

| Reference | Formulation (wt. %) | Remarks |
|---|---|---|
| JHU-001 | 24.5% Pectin<br>30.7% HPMC<br>4.3% Lecithin<br>18.4% Glycerin<br>5.5% Crystal white flavor<br>4.3% Sucralose<br>12.3% Microcrystalline Cellulose | Adjust to remove sweetener (target for no sweetener).<br>Adjust for target disintegration time < 10 sec. |
| JHU-002 | 51.2% Kollicoat® Protect<br>14.3% PVP<br>15.4% Glycerin<br>3.4% Orange flavor<br>4.1% Sucralose<br>1.4% Citric Acid<br>10.2% Microcrystalline Cellulose | Adjust to increase structural integrity.<br>Adjust to remove sweetener (target for no sweetener). |
| JHU-003 | 35.7% Kollicoat® Protect<br>8.6% HPMC<br>10% PVP<br>5.7% Cocoa Butter<br>14.3% Glycerin<br>11.4% Sorbitol<br>5.7% Dextrose<br>8.6% Microcrystalline Cellulose | Adjust to remove sweetener (target for no sweetener).<br>Adjust for target moisture level. |
| JHU-004 | 38.6% Kollicoat® Protect<br>10% PVP<br>28.6% Glycerin<br>22.9% Mannitol | Adjust to remove sweetener (target for no sweetener).<br>Adjust for target moisture level. |
| JHU-005 | 44.7% Kollicoat® Protect<br>55.3% Mannitol | Adjust to increase structural integrity and pliability.<br>Adjust to remove sweetener (target for no sweetener). |
| JHU-006 | 50% Lactose<br>16.7% glycerin<br>33.3% Stearic acid | No binding agent present. Slurry was not formed. |
| JHU-007 | 33.3% HPMC<br>16.7% Lactose<br>16.7% Glycerin<br>33.3% Mannitol | Adjust to increase pliability.<br>Adjust to remove sweetener (target for no sweetener). |
| JHU-008 | 27.6% HPMC<br>17.2% Lactose<br>20.7% Sorbitol<br>34.5% Mannitol | Adjust to increase pliability.<br>Adjust to remove sweetener (target for no sweetener). |
| JHU-009 | 27.6% PVP<br>17.2% Lactose<br>20.7% Sorbitol<br>34.5% Mannitol | Not able to extrude.<br>Adjust to remove sweetener (target for no sweetener). |
| JHU-010 | 100% HPMC | Adjust for target disintegration time < 10 sec. |
| JHU-011 | 20% Kollicoat® Protect<br>80% HPMC | Moisture 2.8%.<br>Adjust for target disintegration time < 10 sec.<br>Adjust pH |
| JHU-012 | 50% Kollicoat® Protect<br>50% HPMC | Moisture 2.5%<br>Adjust for target disintegration time < 10 sec.<br>Adjust pH |
| JHU-013 | 40% Kollicoat® Protect<br>60% HPMC | Moisture 3.5%.<br>Adjust for target disintegration time < 10 sec.<br>Adjust PH. |
| JHU-014 | 60% Kollicoat® Protect<br>40% HPMC | Adjust pH (pH 5.9). |
| JHU-015 | 56.5% Kollicoat® Protect<br>37.7% HPMC<br>5.9% Eudragit® EPO | Adjust pH (pH 6.4). |
| JHU-016 | 100% Kollicoat® Protect | Adjust pH (pH 6.1). |
| JHU-017 | 80% Kollicoat® Protect<br>20% HPMC | Disintegration < 10 s<br>Adjust pH (pH 6.1). |
| JHU-018 | 75% Kollicoat® Protect<br>15% HPMC<br>10% Eudragit® EPO | Adjust pH.<br>Adjust moisture (5.1%) |
| JHU-019 | 70% Kollicoat® Protect<br>20% HPMC<br>10% Eudragit® EPO | Adjust pH (pH 6.4). |
| JHU-020 | 54.4% Kollicoat® Protect<br>35.9% HPMC<br>5.8% Eudragit® EPO<br>0.5% Citric Acid | Adjust pH. |
| JHU-021 | 54.4% Kollicoat® Protect<br>34% HPMC<br>6.0% Eudragit® EPO<br>5.7% Citric Acid | Adjust for taste. |
| JHU-022 | 55.9% Kollicoat® Protect<br>36.9% HPMC<br>6% Eudragit® EPO<br>1.2% Malic Acid | Adjust pH (pH 6.3). |
| JHU-023 | 55% Kollicoat® Protect<br>36.3% HPMC<br>5.9% Eudragit® EPO<br>2.9% Malic Acid | Adjust pH (pH 5.4). |
| JHU-024 | 59.3% Kollicoat® Protect<br>28.9% HPMC<br>5.3% Eudragit® EPO<br>6.6% Pectin | Adjust pH (pH 6.4). |
| JHU-025 | 68.4% Kollicoat® Protect<br>5.3% Eudragit® EPO<br>26.3% Pectin | Adjust pH (pH 6.1). |
| JHU-026 | 58.6% Koillicoat® Protect<br>4.4% Eudragit® EPO<br>32.5% Pectin<br>4.6% Malic Acid | Adjust pH (pH 4.2). |
| JHU-027 | 63.3% Kollicoat® Protect<br>4.7% Eudragit® EPO<br>28.8% Pectin<br>3.7% Malic Acid | Adjust pH (pH 5.4). |
| JHU-028 | 54.1% Kollicoat® Protect<br>35.7% HPMC<br>5.8% Eudragit® EPO<br>4.3% Malic Acid | |
| JHU-029 | 54% Kollicoat® Protect<br>35.5% HPMC<br>5.8% Eudragit® EPO<br>4.7% Malic Acid | Adjust pH (pH 4.3). |
| JHU-030 | 65.7% Kollicoat® Protect<br>29.6% PVP<br>4.7% Eudragit® EPO | Adjust pH (pH 6.1). |
| JHU-031 | 66.3% Kollicoat® Protect<br>24.9% Pectin<br>4.4% Eudragit® EPO<br>4.4% Malic Acid | Adjust pH (pH 5.1). |

-continued

| Reference | Formulation (wt. %) | Remarks |
|---|---|---|
| JHU-032 | 71.7% Kollicoat ® Protect<br>20.2% Pectin<br>4.2% Eudragit ® EPO<br>4.0% Malic Acid | Adjust pH (pH 5.0). |
| JHU-033 | 53.5% Kollicoat ® Protect<br>5.7% Eudragit ® EPO<br>35.3% HPMC<br>4.3% Malic Acid<br>1.11% Sucralose | Moisture 3.98%.<br>Adjust to remove sweetener<br>(target for no sweetener). |
| JHU-034 | 57.9% Kollicoat ® Protect<br>38.2% HPMC<br>4.0% Malic Acid | Adjust for taste. |
| JHU-035 | 57% Kollicoat ® Protect<br>6.3% Pectin<br>27.6% HPMC<br>5.1% Eudragit ® EPO<br>4.1% Malic Acid | Adjust for target disinte-<br>gration time < 10 sec. |
| JHU-036 | 72.2% Kollicoat ® Protect<br>24.2% Pullulan<br>3.6% Malic Acid | pH 5.0.<br>Adjust moisture (4.3%). |
| JHU-037 | 66.2% Kollicoat ® Protect<br>30.1% Pullulan<br>3.7% Malic Acid | pH 4.9.<br>Adjust moisture (4.4%). |
| JHU-038 | 76.4% Kollicoat ® Protect<br>20% Pullulan<br>3.7% Malic Acid | pH 4.8.<br>Adjust moisture (5.2%). |
| JHU-039 | 49% Kollicoat ® Protect<br>40.8% HPMC<br>5.8% Eudragit ® EPO<br>4.3% Malic Acid | |
| JHU-040 | 52% Kollicoat ® Protect<br>44% Pullulan<br>4% Malic Acid | |
| JHU-041 | 54.1% Kollicoat ® Protect<br>35.7% HPMC<br>5.8% Eudragit ® EPO<br>4.3% Citric Acid | Adjust for target disinte-<br>gration time < 10 sec. |
| JHU-042 | 57.9% Kollicoat ® Protect<br>38.2% HPMC<br>4.0% Citric Acid | Adjust for target disinte-<br>gration time < 10 sec. |
| JHU-043 | 77.8% Kollicoat ® Protect<br>18.2% HPMC<br>4.0% Citric Acid | Adjust pH (pH 5.1) |
| JHU-044 | 78.1% Kollicoat ® Protect<br>17.8% HPMC<br>4.2% Citric Acid | Moisture 3.7% |
| JHU-045 | 75% Kollicoat ® Protect<br>15.6% HPMC<br>5% Eudragit ® EPO<br>4.3% Citric Acid | Adjust pH (pH 5.5) |
| JHU-046 | 75.7% Kollicoat ® Protect<br>4.0% Eudragit ® EPO<br>15.8% HPMC<br>4.5% Citric Acid | Moisture 3.9%. |

Example 5: Low Moisture Rapid Dissolving Films, Loss on Drying

Temperature: 200° F.

Sample size: 8 strips

N=3

Procedure: Samples were placed in a beaker and initial weights were recorded. Beakers were placed in the oven. In 30 minute and 1 hour intervals, the beakers were taken out of the oven and placed in a desiccator and cooled to room temperature. Final weights were then recorded and the strips placed back into the oven. The process was repeated until the final weights were consistent.

| Reference | Sample | Moisture Content (wt. %) | Average Moisture Content (wt. %) | Karl Fisher[1] (moisture content) (wt. %) |
|---|---|---|---|---|
| JHU-044<br>78.1% Kollicoat ® Protect<br>17.8% HPMC<br>4.2% Citric Acid | 1<br>2<br>3 | 3.7<br>3.6<br>3.9 | 3.7 | 4.9 |
| JHU-046<br>75.7% Kollicoat ® Protect<br>4.0% Eudragit ® EPO Protect<br>15.8% HPMC<br>4.5% Citric Acid | 1<br>2<br>3 | 3.7<br>4.0<br>3.9 | 3.9 | 5.6 |

[1] Karl Fisher tests were carried out at Micro Quality Labs, Inc. (Burbank, CA).

The invention claimed is:

1. A method of forming an oral dissolvable film, the method comprising:
    (a) contacting water, a rapidly dissolving binder, a film forming polymer, and a moisture deterring polymer, to form a homogeneous mixture comprising a first active ingredient;
    (b) extruding the homogeneous mixture onto a substrate;
    (c) curing the extruded homogeneous mixture to form an orally dissolvable film matrix:
    (d) after the curing of the extruded homogeneous mixture to form the orally disintegrating film matrix, impregnating, via 3D printing, a second active ingredient to the cured oral dissolvable film; and
    (e) sizing the impregnated orally dissolvable film matrix to a desired surface area; wherein,
    the rapidly dissolving binder comprises polyvinyl alcohol (PVA) and polyvinyl alcohol (PVA)-polyethylene glycol (PEG) copolymer;
    the film forming polymer comprises hydroxypropyl methyl cellulose (HPMC);
    the moisture deterring polymer comprises aminoalkyl methacrylate copolymers; and
    the oral dissolvable film has a moisture content of less than 6 wt. %.

2. The method of claim 1, wherein the second active ingredient is moisture sensitive, oxygen sensitive, pH sensitive, heat sensitive, light (UV) sensitive, or any combination thereof.

3. The method of claim 1, wherein the homogeneous mixture in (a) further comprises aminoalkyl methacrylate copolymers.

4. The method of claim 1, wherein the oral dissolvable film has a moisture content of less than 6 wt. % and wherein upon contact with the oral cavity, the oral dissolvable film disintegrates within 15 seconds.

5. The method of claim 1, wherein the homogeneous mixture in (a) further comprises at least one of plasticizer, preservative, solvent, coloring agent, flavoring agent, sweetening agent, filler, bulking agent, saliva stimulating agent, stabilizing and thickening agent, gelling agent, taste masking agent, pigment, lubricant, release modifier, adjuvant, solubilizer & emulsifier, fragrance, emulsifier, surfactant, lipid, glidant, stabilizer, antioxidant, anti-tacking agent, acid, base, buffer, and humectant.

6. The method of claim 1, wherein the oral dissolvable film has a moisture content of less than 4 wt. % and upon contact with the oral cavity, the oral dissolvable film disintegrates within 20 seconds.

7. The method of claim 1, wherein the oral dissolvable film is non-hygroscopic, such that at a glass climatic chamber at 25° C. and at a relative humidity of 60%, the final water content on adsorption after 24 hours is less than 12 wt. %.

8. The method of claim 1, having a content uniformity, such that among two or more samples, the amount of active ingredient ranges from 85% to 115%, with the standard deviation of less than or equal to 6%.

9. The method of claim 1, wherein each active ingredient is independently moisture sensitive, oxygen sensitive, pH sensitive, heat sensitive, light (UV) sensitive, or any combination thereof and wherein the moisture sensitive active ingredient comprises one or more of desmopressin (DDAVP) (D-amino D-arginine vasopressin); dronabinol ((−)-trans-$\Delta^9$-tetrahydrocanniabinol); aspirin (acetylsalicylic acid); penicillin (PCN); dipyridamole; vorapaxar; procaine; atorvastatin; azithromycin; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; methyldopamine; naproxen; acetaminophen; erythromycin; bupropion; rifapentine; penicillamine; mexiletine; verapamil; diltiazem; ibuprofen; cyclosporine; saquinavir; morphine; sertraline; cetirizine; N-[[2-methoxy-5-(1-methyl)phenyl]methyl]-2-(diphenylmethyl)-1-azabicylco[2.2.2]octan-3-amine; adrenaline; amiodarone hydrochloride; atropine sulphate; diazepam; ephedrine; frusemide; haloperidol; lignocaine; metoclopramide; noradrenaline; omeprazole; ondansetron; phenytoin; vercuronium; acyclovir; amoxicillin; cefotetan; cefotaxime; metronidazole; cefuroxime; flucloxacillin; bupivacaine; cilazapril; amlodipine; felodipine; fesoterodine; isradipine; nifedipine; nimodipine; nisoldipine; cyclosporine; saquinavir; itraconazole; and ketoconazole;

the oxygen sensitive active ingredient comprises one or more of dronabinol ((−)-trans-$\Delta^9$-tetrahydrocannabinol); epinephrine (also known as adrenalin or adrenaline); dopamine (3,4-dihydroxyphenethylamine); chlorpromazine (CPZ); captopril; azithromycin; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; methyldopamine; naproxen; acetaminophen; erythromycin; bupropion; rifapentine; penicillamine; mexiletine; verapamil; diltiazem; ibuprofen; cyclosporine; saquinavir; morphine; sertraline; cetirizine; N-[[2-methoxy-5-(1-methyl)phenyl]methyl]-2-(diphenylmethyl)-1-azabicylco[2.2.2]octan-3-amine; adrenaline; amiodarone hydrochloride; atropine sulphate; diazepam; ephedrine; frusemide; haloperidol; lignocaine; metoclopramide; noradrenaline; omeprazole; ondansetron; phenytoin; vercuronium; acyclovir; amoxicillin; cefotetan; cefotaxime; metronidazole; cefuroxime; flucloxacillin; bupivacaine; methylphenidate; fesoterodine fumarate; morphine; hydromorphone; promethazine; dopamine; epinephrine; norepinephrine; esterified estrogen; ephedrine; pseudoephedrine; acetaminophen; ibuprofen; danofloxacin; erythromycin; penicillin; cyclosporine; methyldopate; cetirizine; diltiazem; verapamil; mexiletine; chlorothiazide; carbamazepine; selegiline; oxybutynin; vitamin A; vitamin B; vitamin C; L-cysteine; L-tryptophan; morphine; hydromorphone; promethazine; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; methyldopa; naproxen; acetaminophen; erythromycin; bupropion; rifapentine; penicillamine; mexiletine; verapamil; diltiazem; ibuprofen; cyclosporine; saquinavir; morphine; sertraline; cetirizine; and N-[[2-methoxy-5-(1-methyl)phenyl]methyl]-2-(diphenylmethyl)-1-azabicylco[2.2.2]octan-3-amine;

the pH sensitive active ingredient comprises one or more of desmopressin (DDAVP) (D-amino D-arginine vasopressin); vitamin D3 (cholecalciferol); omeprazole; and esomeprazole;

the heat sensitive active ingredient comprises one or more of dronabinol ((−)-trans-$\Delta^9$-tetrahydrocannabinol); aspirin (acetylsalicylic acid); vitamin D3 (cholecalciferol); diazepam; epinephrine (also known as adrenalin or adrenaline); omeprazole; esomeprazole; and diazepam; and the light (UV) sensitive active ingredient comprises one or more of penicillin (PCN); diazepam; tretinoin; isotretinoin; naproxen; erythromycin; diazepam; haloperidol; acyclovir; amlodipine; isradipine; nifedipine; promethazine; norepinephrine; promethazine; tretinoin; naproxen; digoxin; nitroglycerin; aminophylline; amphotericin B; chlorpheniramine maleate; chlorpromazine HCl; cisplatin; dacarbazine; diazoxide; diphenhydramine; dopamine hydrochloride; doxycycline hyclate; droperidol; epinephrine hydrochloride; fluorouracil; folic acid; furosemide; hydrocortisone; isoproterenol; levarterenol bitartrate; menadiol sodium diphosphate; methadone; morphine sulphate; naloxone; neostigmine methylsulfate; nitroprusside solution; phenylephrine hydrochloride; phytonadione; prochlorperazine edisylate; propranolol hydrochloride; streptomycin sulphate; sulfisoxazole diolamine; terbutaline; testosterone cypionate; triflupromazine hydrochloride; vinblastine; vincristine sulphate; vitamin B complex; dextroamphetamine; ciprofloxacin; clarithromycin; griseofulvin; itraconazole; ketoconazole; terbinafine; tetracycline hydrochloride; 1,4-dihydropyridines; 4-nerolidylcatechol; avobenzone; barnidipine; butyl methoxydibenzoylmethane; doxorubicin; fluoroquinolones; melatonin; naltrexone; cephalosporins; resveratrol; sericin; 3-hydroxyflavone; 4-methylbenzylidene camphor; 5-hydroxyflavones; antazoline; xylometazoline; nafazoline; ascorbic acid; carvedilol; cilnidipine; diclofenac; diflunisal; doxycycline; lansoprazole; manidipine; methotrexate; nicardipine; ofloxacin; oxolinic acid; phenylpropanoids; quercetin; ranitidine; rhein, sulfanilamide; and triprolidine.

10. The method of claim 1, wherein less than 1 mg of the active ingredient per dosage form is impregnated to the cured oral dissolvable film.

11. The method of claim 1, wherein the oral dissolvable film has a thickness of less than 0.120 mm.

12. The method of claim 1, wherein the oral dissolvable film comprises a first and a second active ingredient, wherein the first and the second active ingredient are different, and wherein the second active ingredient is impregnated via 3D printing after the curing of the extruded homogeneous mixture.

* * * * *